United States Patent [19]

Shankar

[11] Patent Number: 5,297,556

[45] Date of Patent: * Mar. 29, 1994

[54] METHOD OF DETECTING ATHEROSCLEROSIS WHILE EXCLUDING MOTION ARTIFACTS

[75] Inventor: Ravi Shankar, Boca Raton, Fla.

[73] Assignee: Florida Atlantic University Research Corp., Boca Raton, Fla.

[ * ] Notice: The portion of the term of this patent subsequent to Sep. 7, 2010 has been disclaimed.

[21] Appl. No.: 98,707

[22] Filed: Jul. 28, 1993

Related U.S. Application Data

[63] Continuation of Ser. No. 9,340, Jan. 26, 1993, Pat. No. 5,241,963, which is a continuation of Ser. No. 715,106, Jun. 12, 1991, abandoned.

[51] Int. Cl.$^5$ .............................................. A61B 5/02
[52] U.S. Cl. .................................... 128/668; 128/693; 128/694; 128/734
[58] Field of Search ................................ 128/691–694, 128/734, 668, 672

[56] References Cited

U.S. PATENT DOCUMENTS

| | | |
|---|---|---|
| 3,577,981 | 5/1971 | Kuris . |
| 3,835,840 | 9/1974 | Mount . |
| 4,144,878 | 3/1979 | Wheeler . |
| 4,432,374 | 2/1984 | Osani . |
| 4,437,469 | 3/1984 | Djordjevich . |
| 4,796,639 | 1/1989 | Snow . |
| 4,870,973 | 10/1989 | Ueno ................................. 128/680 |
| 5,031,637 | 7/1991 | Parra . |
| 5,241,963 | 9/1993 | Shankar ............................. 128/668 |

OTHER PUBLICATIONS

T. M. R. Shankar in "The origin of impedance pulse in the limbs and arterial compliance studies using impedance plethysmography," a Ph.D. Dissertation, Department of Electrical and Computer Engineering, University of Wisconsin, Madison, Wis., 1982. See specifically pp. i, ii, 19, 20, 44–47, 54, 57 & 64.

R. Shankar, M. G. Bond, J. F. Gardin and S. K. Wilmoth, entitled "Noninvasive compliance and morphologic data: An animal study," Proc. Annual Conf. Eng. Biol. Med., vol. 39, pp. 247, 1986.

R. Shankar and M. G. Bond, "Correlation of noninvasive arterial compliance with anatomic pathology of atherosclerotic non-human primates," Poster 852, 8th Int. Symp. Atherosclerosis, Rome, Italy, Oct. 1988.

J. T. Nichol, "The effect of cholesterol feeding on the distensibility of the isolated thoracic aorta," Can. J. Biochem. Physiol., vol. 33, pp. 507–516, 1955.

J. K. Sawyer, M. S. thesis (1984) at the Bowman Gray School of Medicine, Winston-Salem, N.C., entitled "A Comparative Quantitative Study of Atherosclerosis in Abdominal Aorta, Coronary and Carotid Arteries of Hypercholestrolemic Macaca Fascicularis".

L. A. Solberg and J. P. Strong, "Risk Factors and Atherosclerotic Lesions," Arteriosclerosis, vol. 3, pp. 187–198, May/Jun. 1983.

P. Rubba, F. Faccenda, B. De Simone, G. Riccardi and M. Mancini, "Validation of echo-Doppler for the Detection of Iliac Artery Stenosis or Occlusion," in R. J. Hegyeli, ed., End Points for Cardiovascular Drug Studies, vol. 12, Atherosclerosis Reviews, New York: Raven Press, 1984.

(List continued on next page.)

Primary Examiner—Lee S. Cohen
Assistant Examiner—Robert L. Nasser, Jr.
Attorney, Agent, or Firm—Robert C. Kain, Jr.

[57] ABSTRACT

The present invention relates to a method for detecting the onset of atherosclerosis and for detecting the degree of atherosclerosis. Accordingly, one aspect of the present invention correlates data obtained from arteries having a measured amount of stenosis with actual arterial data (blood volume change vs. cuff pressure) obtained from a patient which is converted into data relating to the patient's arterial peak compliance. Another aspect of the present invention detects the onset and the degree of atherosclerosis by classifying the shape of a curve obtained by relating arterial blood volume change with cuff pressure. Two devices can be used, an electrical impedance plethysmograph and a volume plethysmograph.

18 Claims, 17 Drawing Sheets

OTHER PUBLICATIONS

F. M. Abboud, "The role of vascular stiffness in causing or maintaining elevated blood pressure," *Int. Conf. Cardiovascular System Dynamics*, edited by J. Baan, A Noordergraaf, J. Raines, Cambridge, Mass.; MIT Press, 1975.

T. M. R. Shankar and J. G. Webster, "Design of an Automatically Resetting Electrical Impedance Plethysmograph," *J. Clin. Eng.*, vol. 9, p. 129 (1984).

M. G. Bond, S. K. Wilmoth, G. L. Enevold and H. L. Strickland, "Detection and Monitoring of Asymptomatic Atherosclerosis in Clinical Trials," The American Journal of Medicine, vol. 86, Suppl. 4A, Apr. 17, 1989, pp. 33-36.

S. Wallenstein, C. L. Zucker and J. L. Fleiss, "Some statistical methods useful in circulation research," (special article) *Circ. Res.*, vol. 47, pp. 1-9, Jul. 1980.

D. E. Strandness, Jr., "Flow dynamics in circulatory pathophysiology," in *Cardiovascular Flow Dynamics and Measurements*, N. H. C. Hwang and N. A. Normann, Eds. Baltimore: University Park, 1977, pp. 307-334.

Exhibit S1: T. I. Pynadath and D. P. Mukherjee, "Dynamic mechanical properties of atherosclerotic aorta. A correlation between the cholesterol ester content and the viscoelastic properties of atherosclerotic aorta," *Atherosclerosis*, vol. 26, pp. 311-318, 1977. This prior art reference is discussed on p. 1 of the specification.

Exhibit S2: D. J. Farrar, H. D. Green, M. G. Bond, W. D. Wagner and R. A. Gobbee, "Aortic Pulse Wave Velocity, Elasticity, and Composition in a Nonhuman Primate Model of Atherosclerosis," *Circ. Res.*, vol. 43, pp. 52-62, Jul. 1978. This prior art reference is discussed on p. 2 of the specification.

Exhibit S3: D. H. Blankenhorn, S. Brooks, R. H. Selzer, and R. Barndt, Jr., in an article entitled "The Rate of Atherosclerosis Change during Treatment of Hyperlipoproteinemia," *Circulation*, vol. 57, pp. 355-361, Feb. 1978. This prior art reference is discussed on p. 3 of the specification.

Exhibit S4: T. Imura, K. Yamamoto, K. Kanamori, T. Mikami, and H. Yasuda, "Non-invasive ultrasonic measurement of the elastic properties of the human abdominal aorta," *Cardovas. Res.*, vol. 20, pp. 208-214, 1986. This prior art reference is discussed on p. 6 of the specification.

Exhibit S5: R. A. Bomberger, C. K. Zarins and S. Glagov, "Subcritical Arterial Stenosis Enhances Distal Atherosclerosis," *J. Surg. Resch.*, vol. 30, pp. 205-212, 1981. This prior art reference is discussed on p. 12 of the specification.

Exhibit S6: J. F. Cornhill and M. G. Bond, "Morphology: Morphometric Analysis of Pathology Specimens," in: M. G. Bond, W. Insull, Jr., S. Glagov, A. B. Chandler, J. F. Cornhill (eds) *Clinical Diagnosis of Atherosclerosis, Quantitative Methods of Evaluation*, Springer-Verlag, New York, 1983, p. 67. This prior art reference is discussed on p. 24 of the specification.

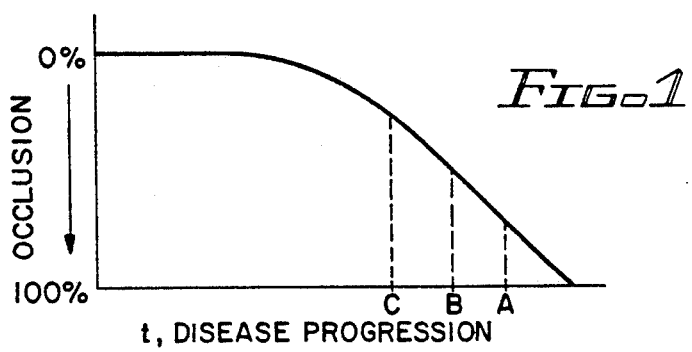
FIG. 1
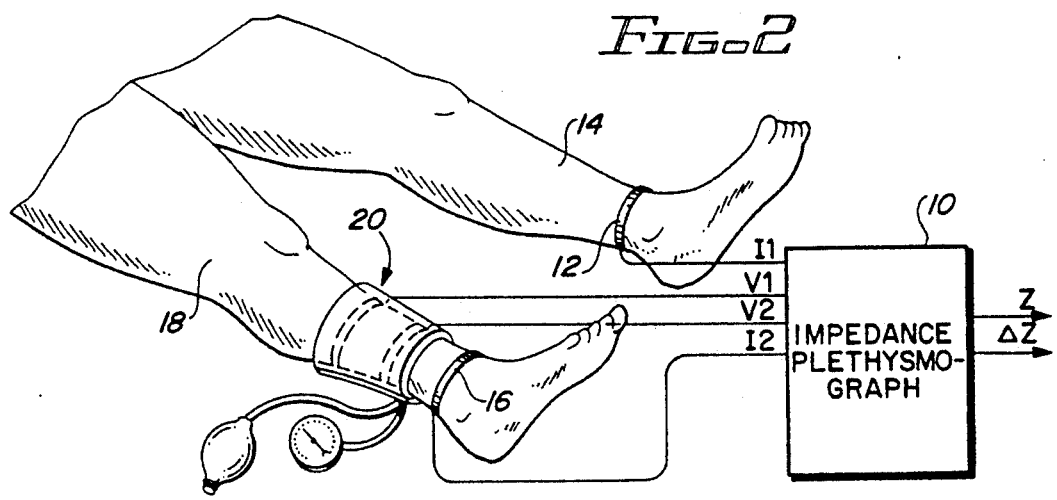
FIG. 2
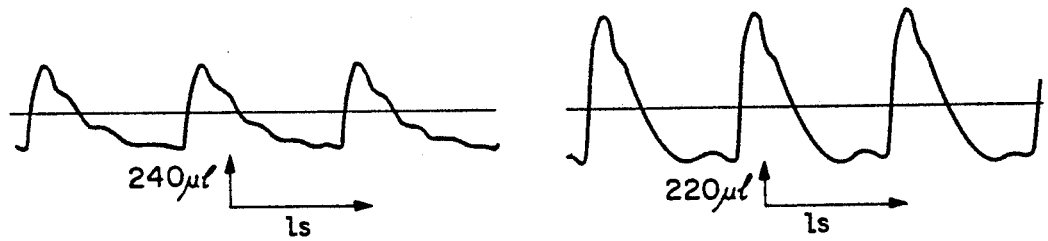
$P_c = 20 \text{ mmHg}, \Delta V = 0.420 \text{ ml}$
FIG. 3A
$P_c = 60 \text{ mmHg}, \Delta V = 0.704 \text{ ml}$
FIG. 3B
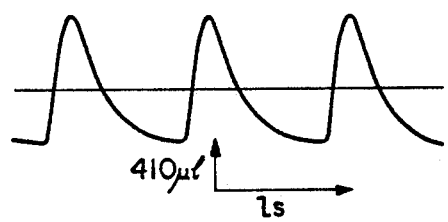
$P_c = 80 \text{ mmHg}, \Delta V = 1.025 \text{ ml}$
FIG. 3C
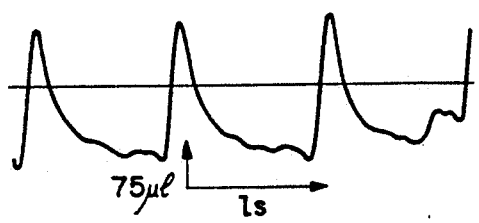
$P_c = 130 \text{ mmHg}, \Delta V = 0.210 \text{ ml}$
FIG. 3D

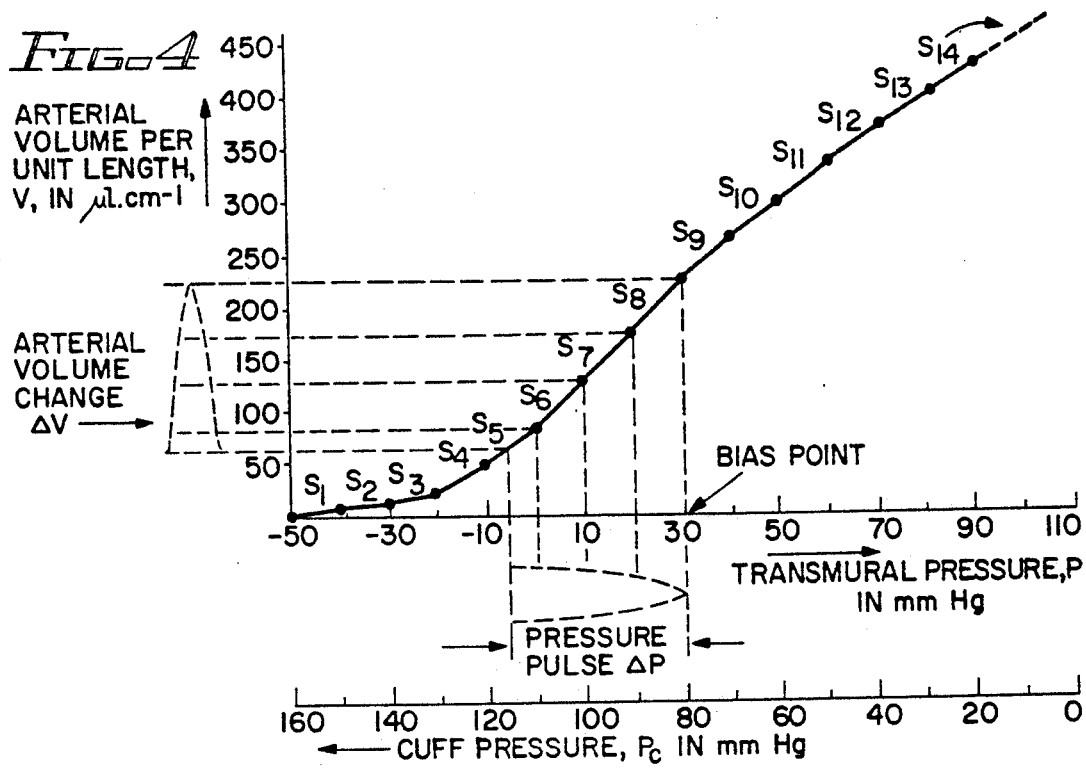
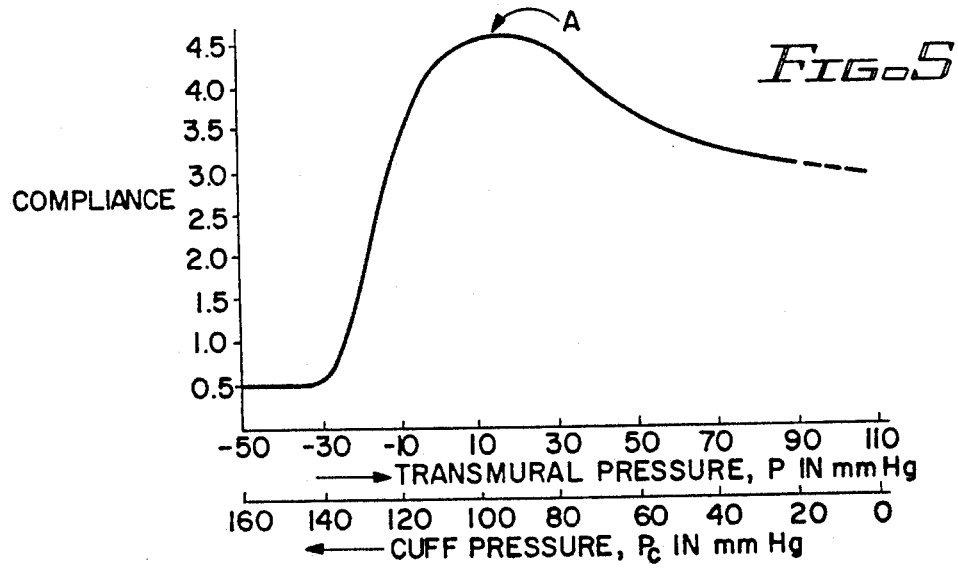

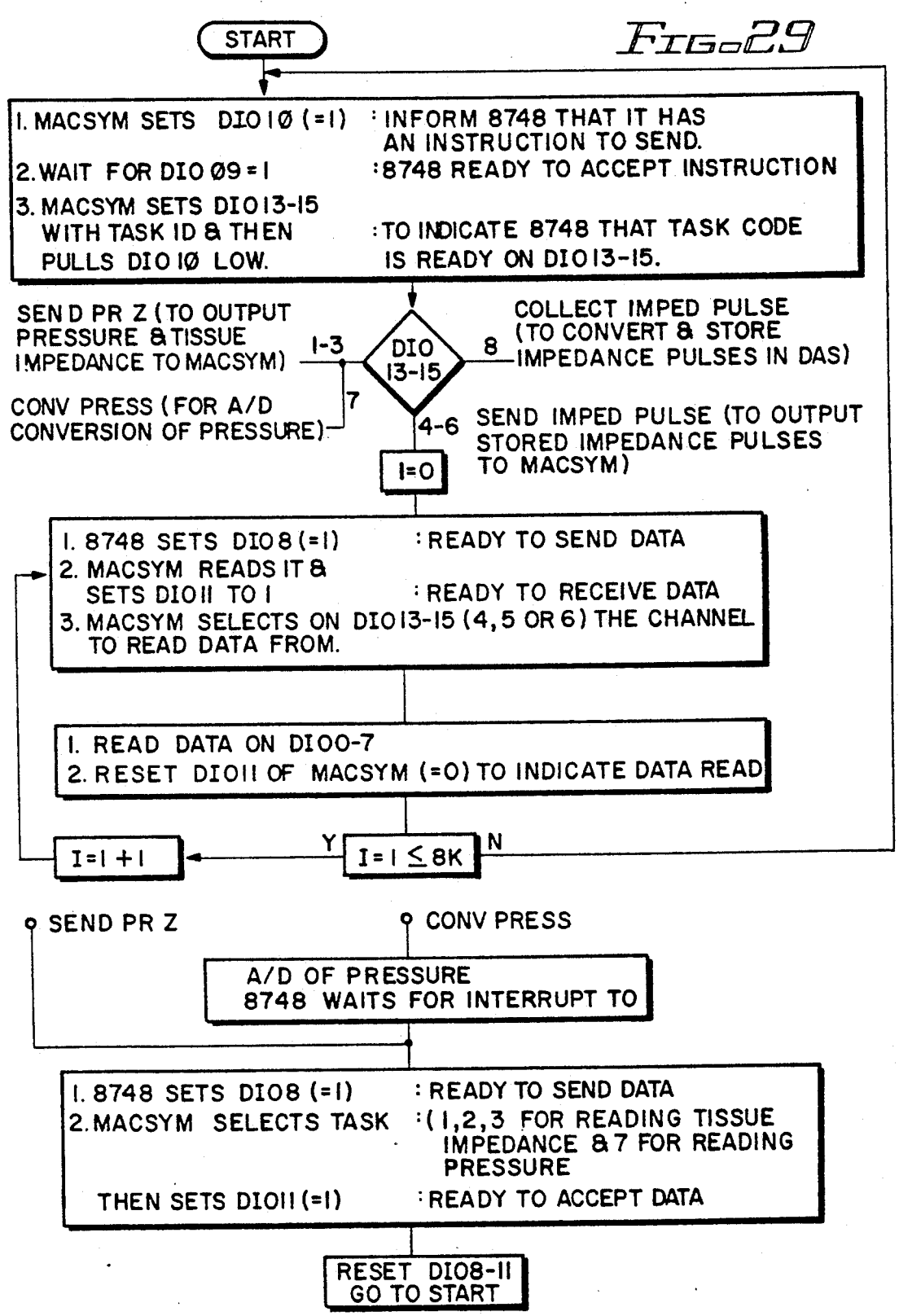

METHOD OF DETECTING ATHEROSCLEROSIS WHILE EXCLUDING MOTION ARTIFACTS

This is a continuation of copending application Ser. No. 08/009,340 filed on Jan. 26, 1993, now U.S. Pat. No. 5,241,963, which is a continuation of application Ser. No. 07/715,106 filed Jun. 12, 1991, now abandoned.

BACKGROUND OF THE INVENTION

The present invention relates to a method and a system for detecting the onset of atherosclerosis and determining the degree of atherosclerosis in a patient by sensing certain physical parameters of the patient's artery. In one embodiment those parameters are correlated with data obtained from arteries having a measured amount of stenosis or closure of the artery, and further correlating the patient's arterial parameter with certain other physical characteristics such as age, blood pressure and cholesterol levels.

Animal studies have shown significant changes in the mechanical properties of arteries with progression of atherosclerosis, a disease commonly referred to in humans as hardening of the arteries. In an article by J. T. Nichol, "The effect of cholesterol feeding on the distensibility of the isolated thoracic aorta," *Can. J. Biochem. Physiol.*, Vol. 33, pp. 507-516, 1955, Nichol determined the effect of cholesterol feeding on the volume-pressure curve of rabbit thoracic aorta. The curves showed a typical characteristic of decreased arterial compliance at higher pressures. He showed that cholesterol feeding of the rabbits decreased peak compliance of vessels during collapse to about 20% of its normal value. An article by T. I. Pynadath and D. P. Mukherjee, "Dynamic mechanical properties of atherosclerotic aorta. A correlation between the cholesterol ester content and the viscoelastic properties of atherosclerotic aorta," *Atherosclerosis*, Vol. 26, pp. 311-318, 1977 (herein Pynadath and Mukherjee) showed that rabbits on a cholesterol diet had a significantly higher tangential Young's modulus compared to the control group during the early stage of disease. For the aorta, the increase was 33% after a period of 6 weeks on a 1.5% cholesterol diet. An article by D. J. Farrar, H. D. Green, M. G. Bond, W. D. Wagner and R. A. Gobbee, "Aortic Pulse Wave Velocity, Elasticity, and Composition in a Nonhuman Primate Model of Atherosclerosis," *Circ. Res.*, Vol. 43, pp. 52-62, July 1978, (herein Farrar et al.) discloses a study of 13 monkeys (*Macaca fascicularis*) which were fed either an atherogenic or control diet for 36 months. They found that the aortic pulse wave velocity in the atherosclerotic monkeys was 1.5 to 2 times the values for the control animals. With postmortem studies, they found that the static circumferential distensibility of the excised atherosclerotic aortas was significantly less than the control, but there was no difference in incremental (Young's) modulus of elasticity. They concluded that the significantly increased stiffness of the atherosclerotic arteries appeared to be mainly due to the increased wall thickness caused by the atherosclerotic plaques and perhaps due to extensive medial damage, rather than due to material changes described by Young's modulus. Though Pynadath and Mukherjee and Farrar et al. differed in their conclusion with regard to the changes in the Young's modulus, both results imply stiffer arteries, which were more resistant to collapse and had lower compliance during collapse.

In addition to detection of atherosclerosis, intervention studies of risk factor reduction in humans have been undertaken to determine the extent of regression, if any, with different intervention regimens combining dietary modification, drugs, and exercise programs A similar conclusion was drawn in an animal study conducted (on abdominal, carotid and coronary arteries) by J. K. Sawyer, as reported in her M.S. thesis (1984) at the Bowman Gray School of Medicine, Winston-Salem, N.C., entitled "A Comparative Quantitative Study of Atherosclerosis in Abdominal Aorta, Coronary and Carotid Arteries of Hypercholestrolemic *Macaca fascicularis.*" Serial comparison of individual human data is not possible because epidemiologic end points, such as cardiovascular death, significantly affect the data. Serial data for humans is extremely difficult to evaluate when other epidemiological end points are identified, such as myocardial infarction and stroke. The occurrence of myocardial infarction in a human implies that vascular insufficiency has grown worse, and there is no corresponding end point which can be selected to ascertain whether vascular insufficiency has improved. D. H. Blankenhorn, S. Brooks, R. H. Selzer, and R. Barndt, Jr., in an article entitled "The Rate of Atherosclerosis Change during Treatment of Hyperlipoproteinemia," *Circulation*, Vol. 57, pp. 355-361, February 1978, advocate the use of femoral angiograms (an invasive imaging technique) for serial comparison of lesion size. The relationship of femoral lesion change to long-term cardiovascular mortality rate, however, is not fully known at present. Even though the severity of atherosclerosis in one artery does not predict the severity in another artery for an individual case, on a group basis, the average amount of lesion development in one artery can be correlated with the average amount of lesion involvement in other arteries. See L. A. Solberg and J. P. Strong, "Risk Factors and Atherosclerotic Lesions," *Arteriosclerosis*, Vol. 3, pp. 187-198, May/June 1983. Researchers have continued to evolve techniques to obtain and decipher electronic images of superficial arteries, such as carotid and femoral arteries, since early detection of atherosclerosis and implementation of an intervention program to reduce atherosclerosis even in one vascular bed may improve the quality of life, reduce economic burdens inherent with atherosclerosis, and prolong the life span of the patient.

Selective angiography, using invasive equipment and electronic imaging techniques, involves significant cost, plus some discomfort and risk to patients. This has led to the development of B-mode ultrasound for noninvasive observation of lesions in the carotid artery and related electronic imaging techniques to evaluate the electronically obtained vascular image. See M. G. Bond, W. A. Riley, R. W. Barnes, J. M. Kaduck, and M. R. Ball, "Validation Studies of a Noninvasive Real Time B-scan Imaging System," in T. F. Budinger, A. S. Berson, I. Ringquist, M. B. Mock, J. T. Watson, and R. S. Powell, eds., *Noninvasive Techniques for Assessment of Atherosclerosis in Peripheral, Carotid, and Coronary Arteries*, pp. 197-203, New York: Raven Press, 1982. The National Heart, Lung and Blood Institute the National Institute of Health has initiated a multicenter study which is currently under way to enhance the sensitivity, specificity and signal processing techniques required to perfect B-mode ultrasound detection of the disease. Also, computerized fluoroscopy is an experimental, minimally invasive imaging technique that is being used to characterize arterial lesions. See C. A. Mistretta, R.

A. Kruger, D. E. Ergun, C. G. Shaw, M. Van Lysel, C. Strother, A. B. Crummy, J. F. Sackett, W. Zwiebel, D. Myerowitz, W. Turnipseed, and H. Berkoff, Intravenous Angiography Using Fluoroscopy Techniques, in T. F. Budinger, A. S. Berson, Ringquist, II, M. B. Mock, J. T. Watson, and R. S. Powell, eds., *Noninvasive Techniques for Assessment of Atherosclerosis in Peripheral, Carotid and Coronary Arteries*, p. 71, Raven Press, New York (1984).

Noninvasive techniques for early detection of atherosclerosis are currently being developed with a corresponding ability to follow progression/regression of the disease in humans. These techniques are thus becoming increasingly essential, as new intervention techniques are continually evolving and as the public becomes increasingly aware of the effects of lifestyle on their quality and length of life.

While the electronic imaging techniques have tried to focus on lesions, other techniques have evolved that address the hemodynamic effects and changes in mechanical properties associated with atherosclerosis. Recently an echo-doppler examination coupled with spectral analysis signal processing techniques has been used to study iliac artery stenosis. See P. Rubba, F. Faccenda, B. De Simone, G. Riccardi and M. Mancini, "Validation of echo-Doppler for the Detection of Iliac Artery Stenosis or Occlusion," in R. J. Hegyeli, ed., *End Points for Cardiovascular Drug Studies*, Vol. 12, Atherosclerosis Reviews, New York: Raven Press, 1984. These authors indicate that the method has many potential sources of errors and much work is needed before the technique is widely accepted and its routine adopted by the medical community. An echo tracking device coupled to B-mode ultrasound equipment has been used to measure the elastic properties of the human abdominal aorta. See T. Imura, K. Yamamoto, K. Kanamori, T. Mikami, and H. Yasuda, "Non-invasive ultrasonic measurement of the elastic properties of the human abdominal aorta," *Cardovas. Res.*, Vol 20, pp. 208-214, 1986. Imura et al. found that $E_p$, the pressure strain elastic modulus, was significantly higher in subjects older than 60 years.

The theory of detecting atherosclerosis based on noninvasive determination of arterial compliance in the leg was studied by T. M. R. Shankar in "The origin of impedance pulse in the limbs and arterial compliance studies using impedance plethysmography," a Ph.D. Dissertation, Department of Electrical and Computer Engineering, University of Wisconsin, Madison, Wis., 1982 (herein the Shankar thesis). The Shankar thesis discloses that the arterial peak compliance in humans decreases with age, hypertension and further decreases with peripheral vascular disease.

In the Shankar thesis, an electrical impedance plethysmography (ZPG) was used to record the impedance pulse $\Delta Z$ due to pulsatile blood flow through the artery under study. The impedance pulse was used to calculate the arterial pulse volume $\Delta V$. Further, the compliance value C of the artery under study was computed as the ratio of $\Delta V$ to the blood pressure pulse $\Delta P$ (obtained using the Korotkoff method: systolic minus phase 5 diastolic pressure). To obtain C at different arterial transmural pressures, a pressure cuff was wrapped around the lower leg of the patient and the cuff pressure was incrementally increased while the impedance pulse was measured. At an external cuff pressure of about 100 mm Hg (slightly higher than the diastolic pressure), the transmural pressure of the artery was near zero and the maximal arterial volume change was recorded. The arterial walls are most flaccid at zero transmural pressure. The maximum ratio of $\Delta V$ and $\Delta P$ provides the maximal (or peak) compliance $C_p$. This technique was used to study 118 human subjects. The findings revealed that $C_p$ varied significantly with risk factors for atherosclerotic cardiovascular disease.

In the follow-up pathologic validation study, 20 monkeys were studied. Preliminary results were presented in an article by R. Shankar, M. G. Bond, J. F. Gardin and S. K. Wilmoth, entitled "Noninvasive compliance and morphologic data: An animal study," *Proc. Annual Conf. Eng. Biol. Med.*, Vol. 39, pp. 247, 1986 (herein the Shankar '86 study) and in R. Shankar and M. G. Bond, "Correlation of noninvasive arterial compliance with anatomic pathology of atherosclerotic non-human primates," Poster 852, 8th Int. Symp. Atherosclerosis, Rome, Italy, October, 1988 (herein the '88 Poster). Respective groups of monkeys were fed a cholesterol diet and a control diet for a period of 26 months. The results disclosed in the Shankar '86 study revealed that there was a negative correlation between the peak compliance and the averaged percent of intima in arterial tissue The results indicate a distinct inverse association for arteries between the absolute amount of atherosclerotic plaque and the peak compliance. However, the Shankar '86 study noted that the correlation was only a rank correlation, that the morphometric measurements were worst case values, and those measurements were not necessarily the values for the arterial section subjected to the non-invasive measurements The '88 Poster revealed a correlation between the non-invasively measured peak compliance of the monkeys and the actual morphometric data and concluded that (1) peak compliance was significantly lower in atherosclerotic arteries, and (2) peak compliance may be an approximate measure to detect early atherosclerosis.

The method of the present invention is related, in a most general sense, to the invasive procedure adopted by Abboud to determine arterial rigidity. See F. M. Abboud, "The role of vascular stiffness in causing or maintaining elevated blood pressure," *Int. Conf. Cardiovascular System Dynamics*, edited by J. Baan, A. Noordergraaf, J. Raines, Cambridge, Mass.; MIT Press, 1975. Abboud estimated stroke volume using ballistocardiography. He assumed that the arterial volume change was a fixed fraction of the stroke volume. He used an intra-arterial catheter placed in the brachial artery to measure the pressure He induced vasodilation in human subjects with amyl nitrite inhalation. This resulted in a slow decrease in the arterial pressure The pulse pressure also decreased, which indicated a higher compliance. Arteries showed a higher rigidity index (a lower peak compliance) with aging. Subjects with clinical symptoms of atherosclerosis had still higher values of rigidity index.

The method of the present invention is also generally related to two other noninvasive techniques: the oscillometric method of blood pressure measurement and pulse volume recording (PVR). In the oscillometric method, a pressure cuff is wrapped around the arm and the cuff pressure oscillations are recorded as the cuff pressure is decreased from suprasystoic or subdiastolic pressure. The oscillations start at systolic pressure, and the amplitude of oscillations increases, reaching maximum near the mean pressure and gradually decreasing below that mean pressure. See generally L. A. Geddes, *The Direct and Indirect Measurement of Blood Pressure*, Chicago: Year Book Medical Publishers, 1970. The oscillations are proportional to volume changes. If the volume of the air in the cuff is known, one can obtain calibrated volume changes, which should equal values obtained with the impedance plethysmograph. This has been verified for cuff pressures near the mean pressure, where the maximal arterial volume change (and hence $C_p$) is obtained. The difference between outputs from the volume and impedance plethysmographs was typically 3% for leg segments.

Pulse volume recording (PVR) is widely used for the evaluation of subjects with peripheral vascular disease. See R. F. Kempczinski and J. S. T. Yao (eds), *Practical Noninvasive Vascular Diagnosis*, Chicago: Year Book Medical Publishers, 1987. PVR uses a segmental plethysmograph. In an article by L. H. Griffin, Jr., C. H. Wray and W. H. Moretz, "Immediate assessment of vascular operations using segmental plethysmography," *Am. Surgeon*, Vol. 41, pp. 67-76, 1975), a standardizing device was used. However, this practice does not seem to be common. PVR is mainly used to monitor qualitative changes with progression of peripheral vascular disease. The recording is made at one cuff-pressure, 65 mm Hg, which is typically less than diastolic pressure and where maximal arterial volume change is not recorded.

U.S. Pat. No. 3,835,840 to Mount discloses an apparatus and a method for non-invasive measurement of volume rate of flow of blood in an artery. A plethysmograph imparts an excitation to a pair of outer electrodes, bound about a leg or arm, and a pair of inner electrodes are connected to a voltage sensor in the plethysmograph. The plethysmograph outputs a signal which is directly proportional to the impedance of the appendage bound between the electrodes. An electrical circuit produces an output value that is essentially proportional to pulsatile arterial flow by taking the time derivative of the plethysmograph output, providing a zero reference value and then integrating the result over a predetermined time. The Mount disclosure states that the accuracy of this system decreases due to hypertension or arterial wall stiffening (arteriosclerosis).

U.S. Pat. No. 4,432,374 to Osanai discloses a plethysmographic acceleration pulse wave meter which measures the increase or decrease in blood volume through a finger apex. The output of a plethysmograph is twice or triply differentiated to produce an acceleration curve.

U.S. Pat. No. 4,144,878 to Wheeler discloses an occlusive impedance plethysmograph. The rate at which blood flows out from the venous system immediately following cessation of the forced blockage of the venous return to the heart (venous outflow rate) is correlated with the change in venous volume which accompanies the application of the force blockage (venous capacitance).

U.S. Pat. No. 4,437,469 to Djordjevich discloses a system for determining characteristics of blood flow. An impedance plethysmograph is utilized and the signal output therefrom is graphically compared to a signal representing blood pressure changes.

U.S. Pat. No. 3,577,981 to Kuris discloses an ultrasonic method for detecting the accumulation of cholesterol.

SUMMARY OF THE INVENTION

The present invention relates to a method for detecting the onset of atherosclerosis and for detecting the degree of atherosclerosis. Although the prior art discloses that peak compliance decreases with age and other risk factors, previously it was not possible to ascertain the degree of atherosclerosis. Accordingly, one aspect of the present invention correlates data obtained from arteries having a measured amount of stenosis with actual data obtained from a patient which is converted into data relating to the patient's arterial peak compliance. Another aspect of the present invention detects the onset and the degree of atherosclerosis by classifying the shape of a curve obtained by relating arterial blood volume change with cuff pressure.

There are two devices which can be used to obtain arterial data from a patient. One device is an electrical impedance plethysmograph and the other is a volume plethysmograph.

The correlation between the patient's peak compliance and comparison data (representing the measured amount of stenosis of an artery) was obtained using Pearson correlation coefficients. The comparison data representing the measured amount of stenosis in an artery was obtained from a study of monkeys. Statistically significant mathematical correlations were found between the non-invasively obtained peak compliance data (obtained bilaterally at the upper thigh level prior to sacrifice of a group of monkeys) and the morphometric data obtained bilaterally postmortem from the iliac and carotid arteries of the monkeys. The percentage intima in arterial tissue (PIAT) is a morphometric measure that has been identified by other researchers as a significant indicator of atherosclerosis. J. K. Sawyer, "A comparative quantitative study of atherosclerosis in abdominal aorta, coronary and carotid arteries of hypercholesterolemic *Macaca fascicularis*, M.S. Thesis, Bowman Gray School of Medicine, Winston-Salem, N.C., 1984.

Five of the monkeys were surgically coarcted at the level of thoracic aorta. A large pressure gradient exists across such a coarctation, resulting in significant differences in atherosclerosis on two parts of the arterial system. See R. A. Bomberg, C. K. Zarins and S. Glagov, "Subcritical Arterial Stenosis Enhances Distal Atherosclerosis," *J. Surg. Resch.*, Vol. 30, pp. 205-212, 1981.

With coarcted animals excluded, the Pearson correlation coefficient between averaged PIAT and the peak compliance was found to be $-0.52$, at a level of significance of 0.01, for measurements from 27 limbs. See R. Shankar and M. Gene Bond, "Correlation of noninvasive arterial compliance with anatomic pathology of atherosclerotic nonhuman primates," *Atherosclerosis*, Vol. 85, pp. 37-46, December 1990. The peak compliance in these studies was determined with both electrical impedance plethysmography (ZPG) and volume plethysmography (VPG).

The peak compliance data, computed from measurements conducted on arteries in the left and right legs, with a ZPG and VPG respectively, were within a few percent of each other, for several monkeys.

The correlations from the monkey study are linked in the present invention to correlations obtained from a human study. The human study revealed a good mathematical correlation between peak arterial compliance and systolic pressure, age and tissue impedance. By combining these two mathematical relationships (one derived from the monkey study, the other from the human study), the present invention provides a method and a system to quantify the degree of atherosclerosis. Additionally, the monkey study data revealed a new correlation between blood volume change, cuff pressure and atherosclerosis. This new correlation s based upon waveform shape classification which can predict the onset of atherosclerosis as well as the degree of atherosclerosis.

OBJECTS OF THE INVENTION

It is an object of the present invention to detect the onset of atherosclerosis.

It is another object of the present invention to detect and quantify the degree of atherosclerosis.

It is a further object of the present invention to non-invasively sense certain physical parameters of a patient or subject under study, to wit, the flow of blood through an artery and correlate that data with known arterial data, in order to quantify the degree of atherosclerosis for that patent; the degree of atherosclerosis being further related to certain factors such as the patient's age, blood pressure, etc.

BRIEF DESCRIPTION OF THE DRAWINGS

Further objects and advantages of the present invention can be found in the detailed description of the preferred embodiments when taken in conjunction with the accompanying drawings in which:

FIG. 1 diagrammatically illustrates arterial occlusion versus the time or atherosclerotic disease progression.

FIG. 2 schematically illustrates an electrical impedance plethysmograph (ZPG) coupled to the legs of a human.

FIGS. 3a, b, c and d illustrate a typical set of arterial flow recordings at selected cuff pressures.

FIG. 4 diagrammatically illustrates the relationship between arterial blood volume and either transmural pressure or cuff pressure.

FIG. 5 is a compliance-pressure curve derived from FIG. 4.

Figure 8A:
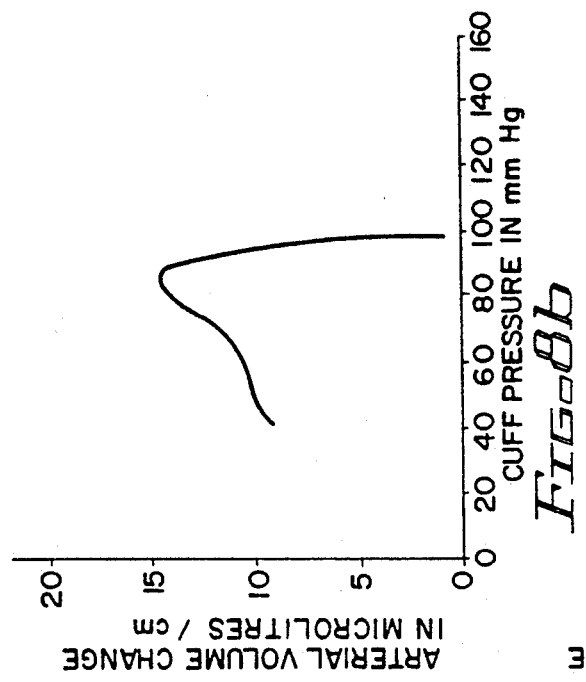

The graphs of FIGS. 8a, b, c, and d plot the measured arterial volume change (for example, the blood volume differential through the artery) against the cuff pressure (for the left thighs) for four different monkeys.

Figure 9:
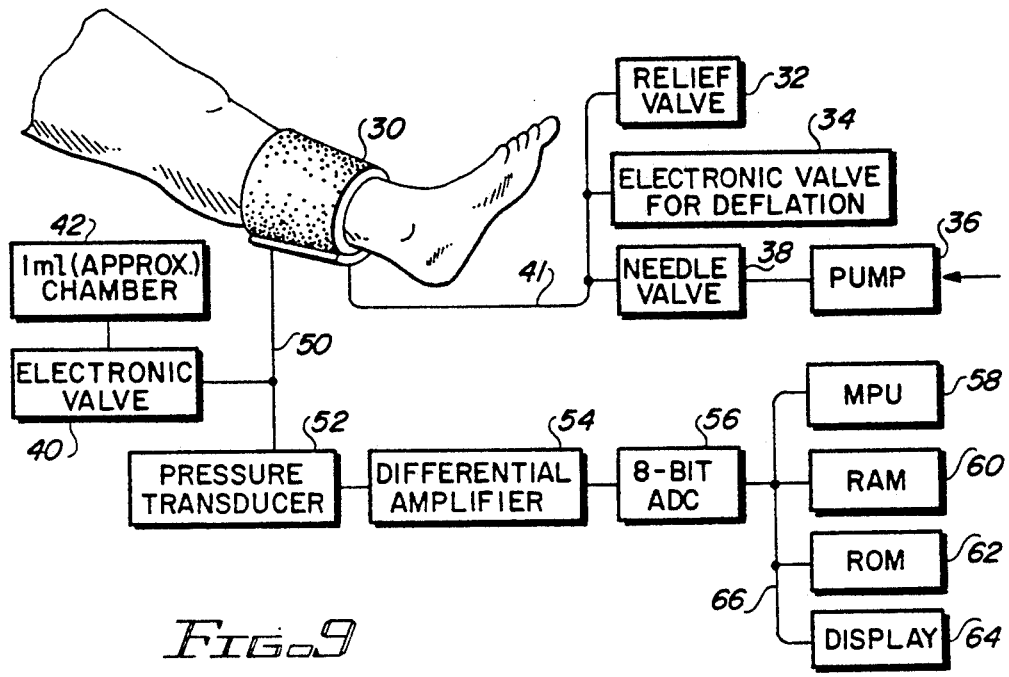

FIG. 9 is a block diagram illustrating a volume plethysmograph.

FIG. 10 is a structure diagram for the volume plethysmograph.

Figure 11:
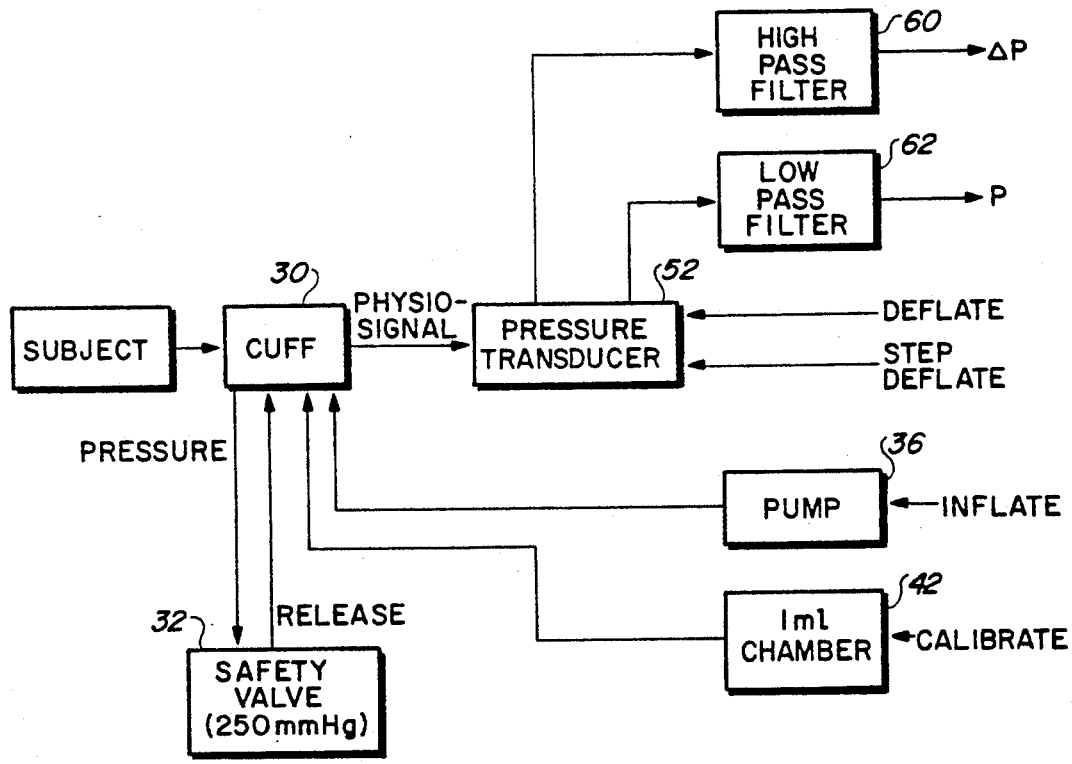

FIG. 11 diagrammatically illustrates the pneumatic/electronic interface of the volume plethysmograph.

Figure 12:
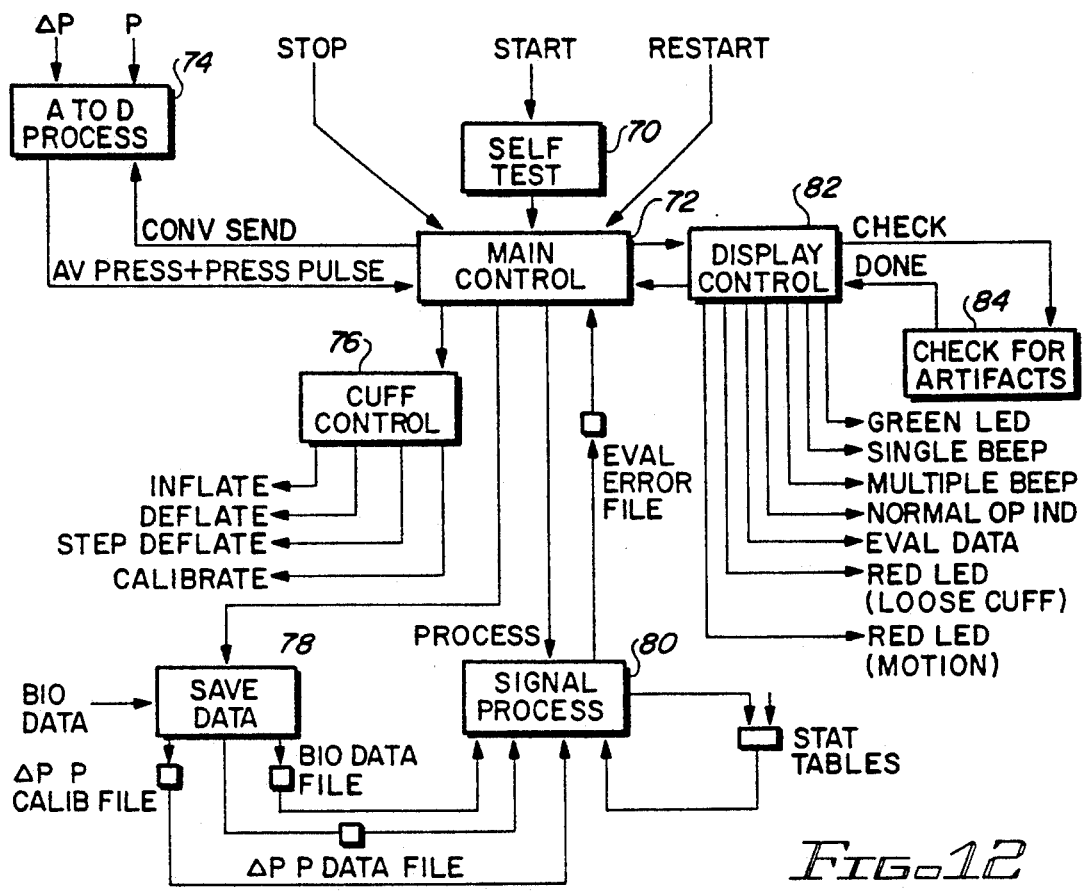

FIG. 12 is an electronic structured diagram for the volume plethysmograph.

Figure 13:
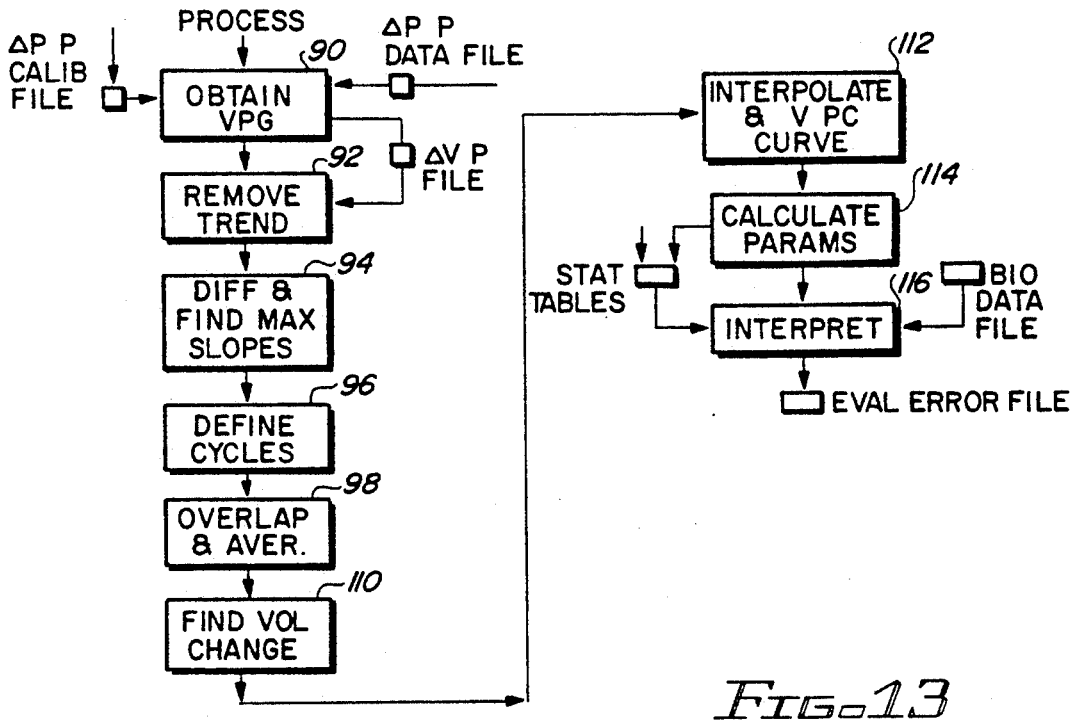

FIG. 13 is a structured diagram showing the principal processes for the volume plethysmograph.

Figure 14:
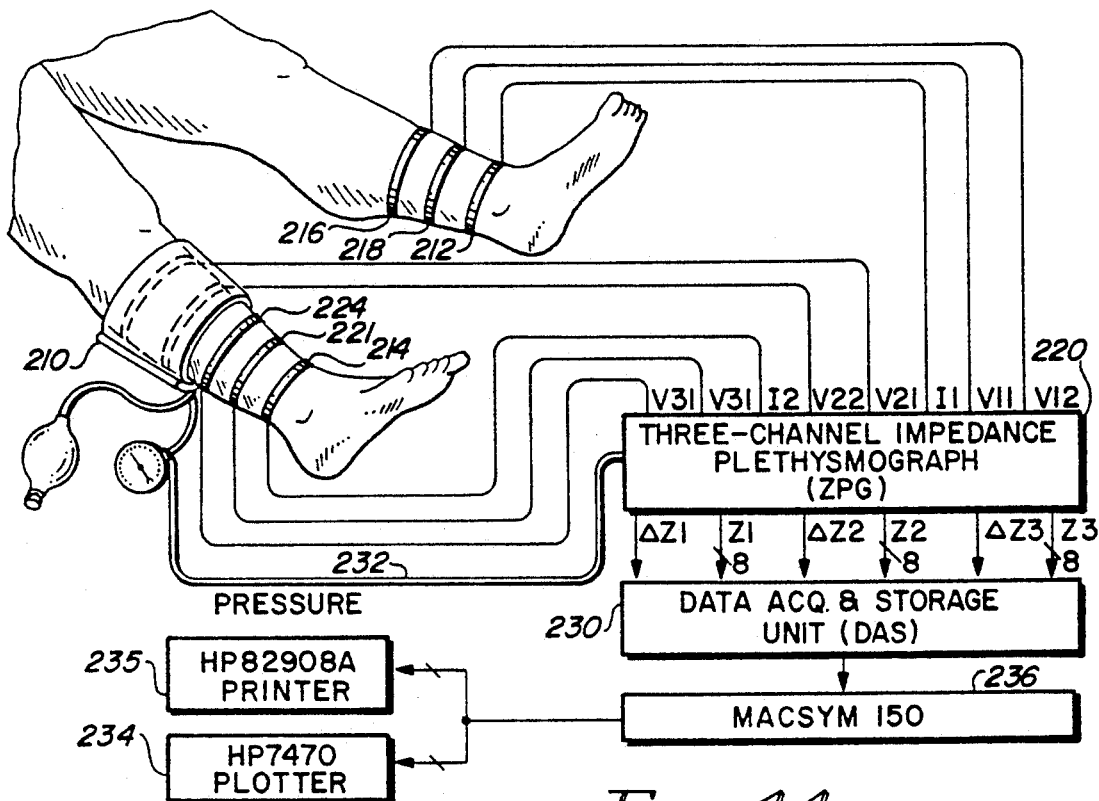

FIG. 14 illustrates an enhanced system using an electrical impedance plethysmograph with a computerized signal processing system.

Figures 15, 16:
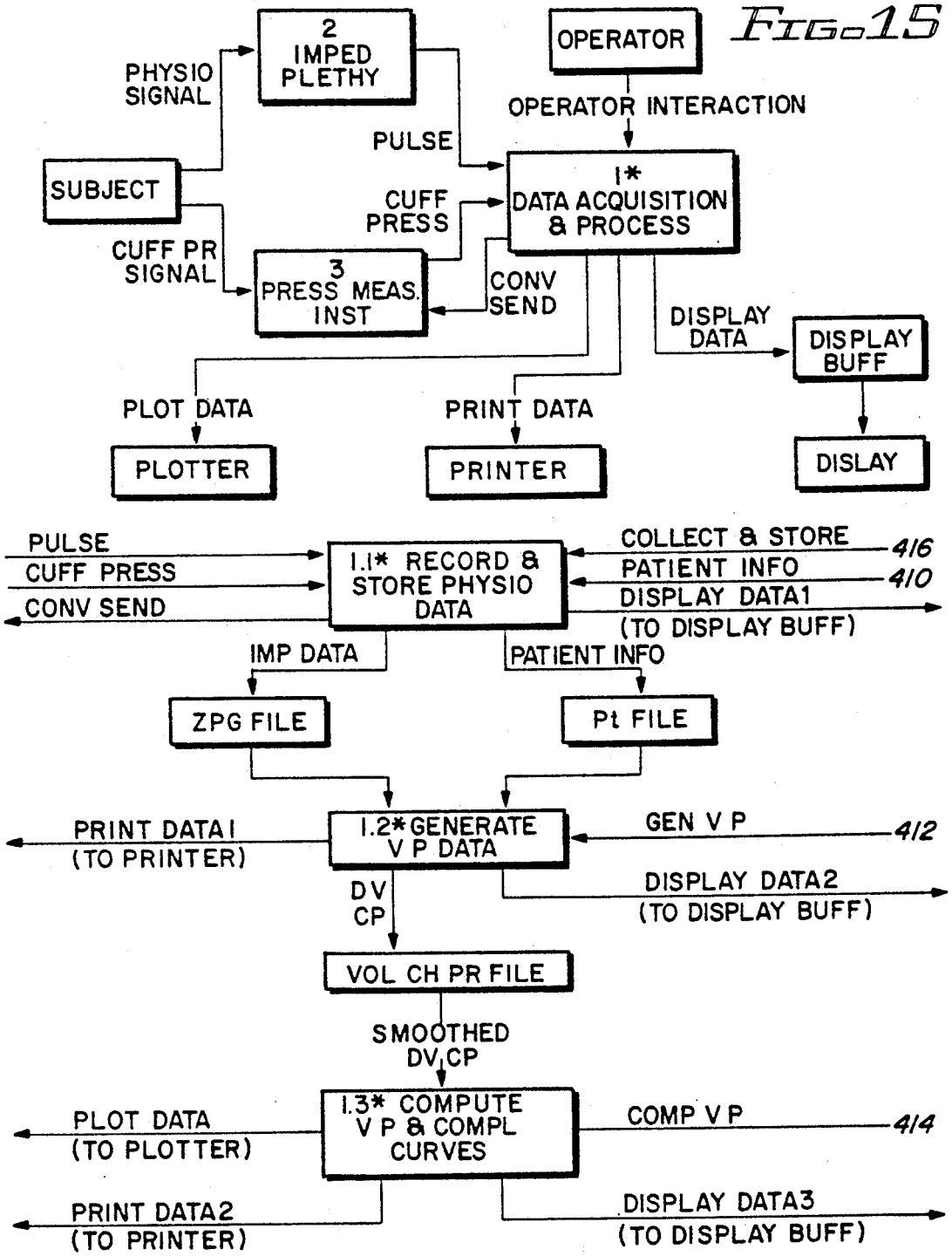

FIG. 15 illustrates a top level data flow diagram of the system illustrated in FIG. 14.

FIG. 16 illustrates an intermediate level data flow diagram.

Figure 17:
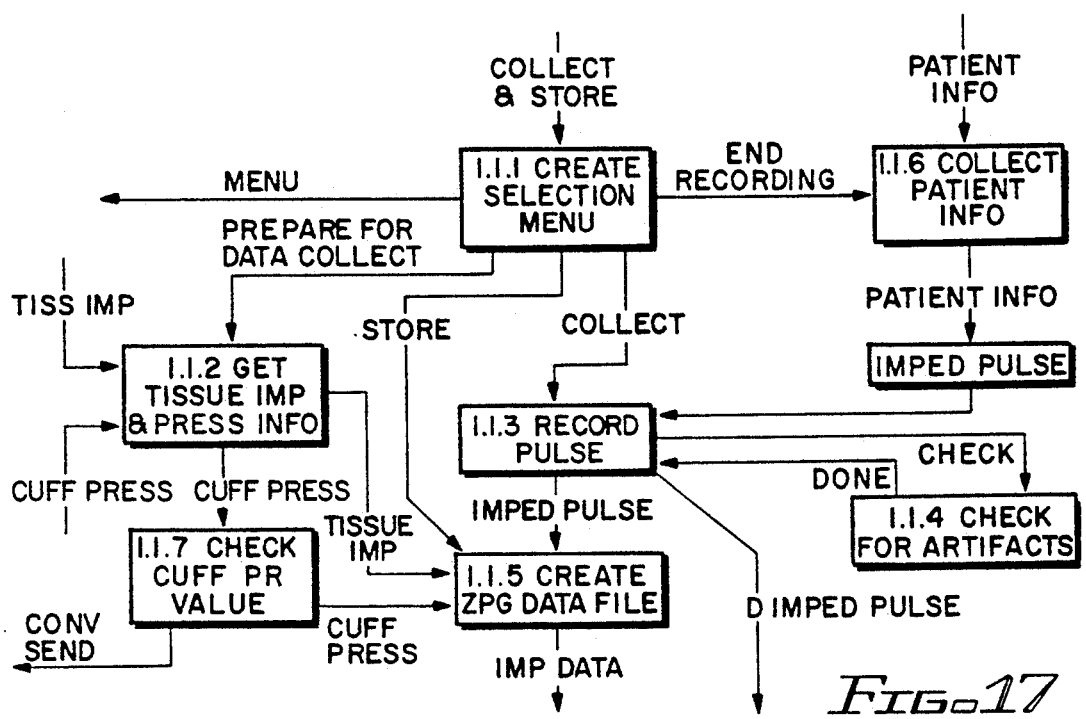

FIG. 17 illustrates a low level data flow diagram of data acquisition.

Figure 18:
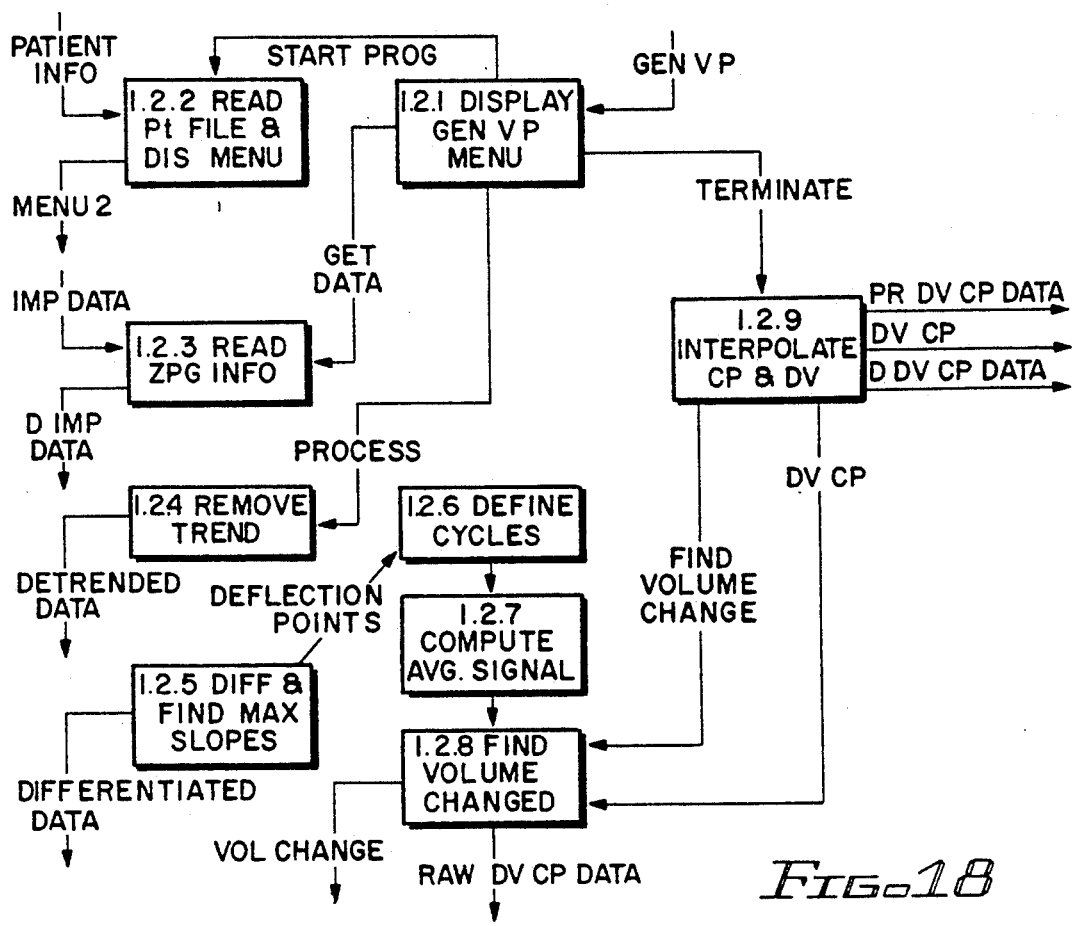

FIG. 18 illustrates a low level data flow diagram of data processing.

Figure 19:
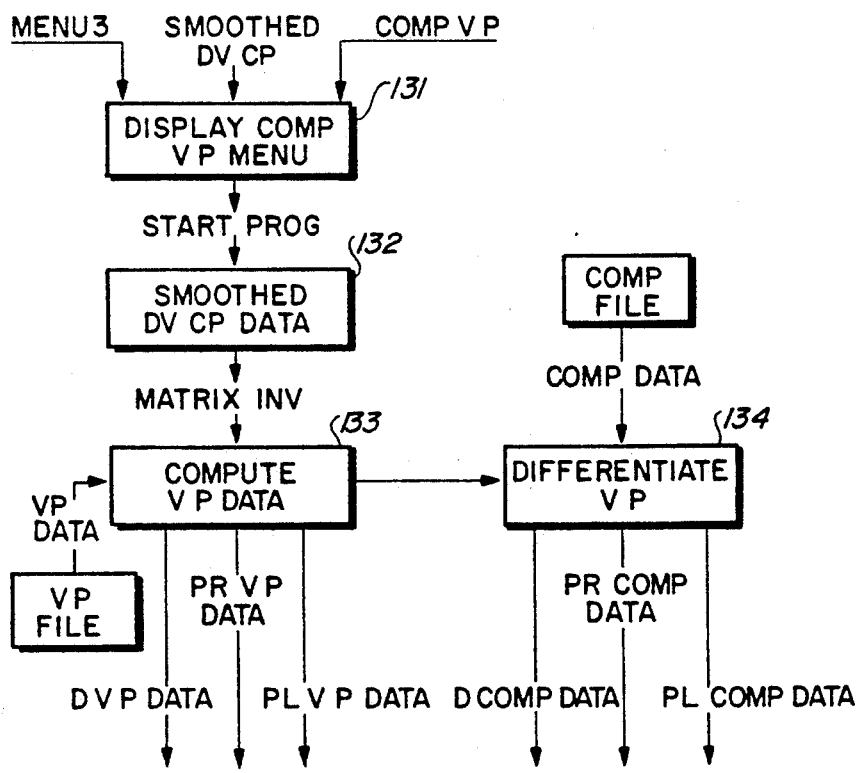

FIG. 19 illustrates a low level data flow diagram of data processing continued from FIG. 18.

Figure 20A:
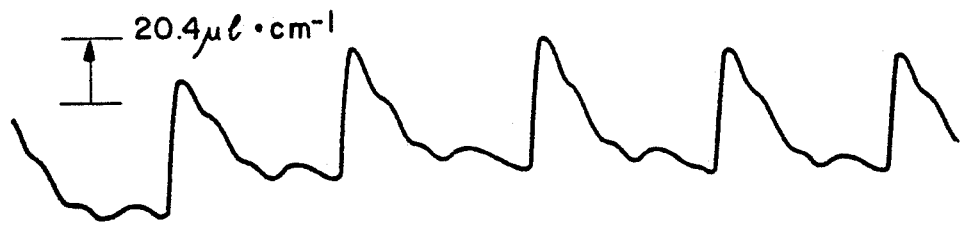

FIGS. 20a, b, c and d illustrate signal processing in the system, to wit, (a) illustrates an acquired signal, (b) illustrates a moving average, (c) illustrates the signal after de-trending, and (d) illustrates the signal after differentiation.

Figure 21:
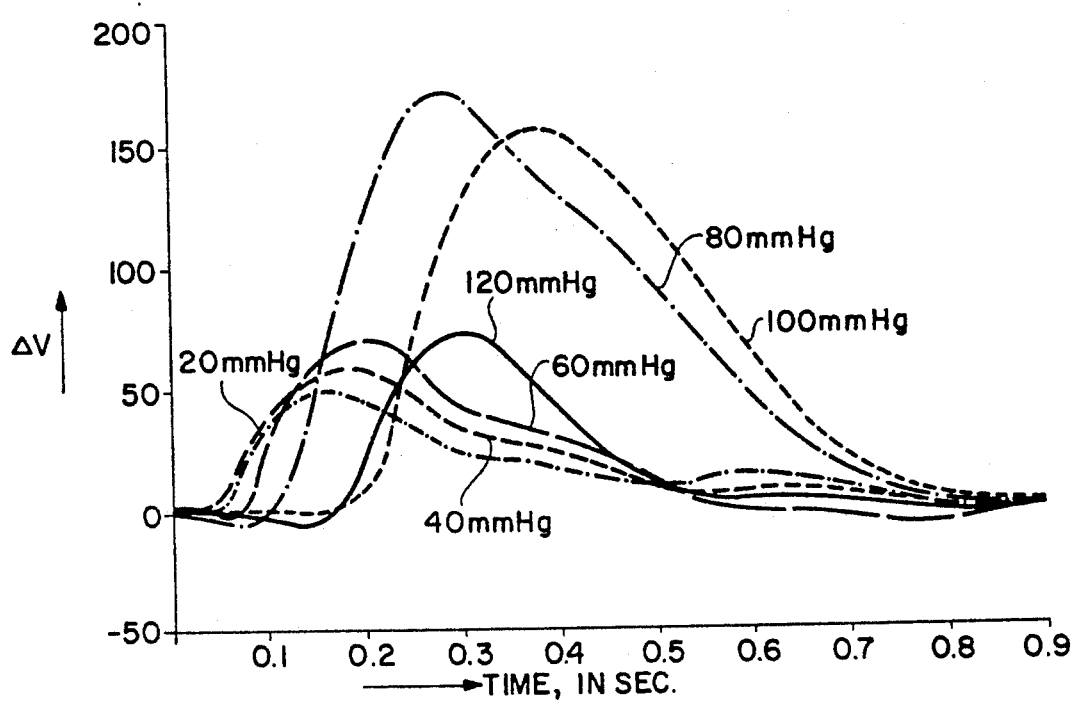

FIG. 21 illustrates volume pulse recordings from a limb segment under a pressure cuff, for various cuff pressures in the range of 20-120 mm Hg. Each is the average of 5-6 cycles. Signals at different cuff pressures have been overlapped with the aid of simultaneously acquired ECG as time reference.

Figure 22:
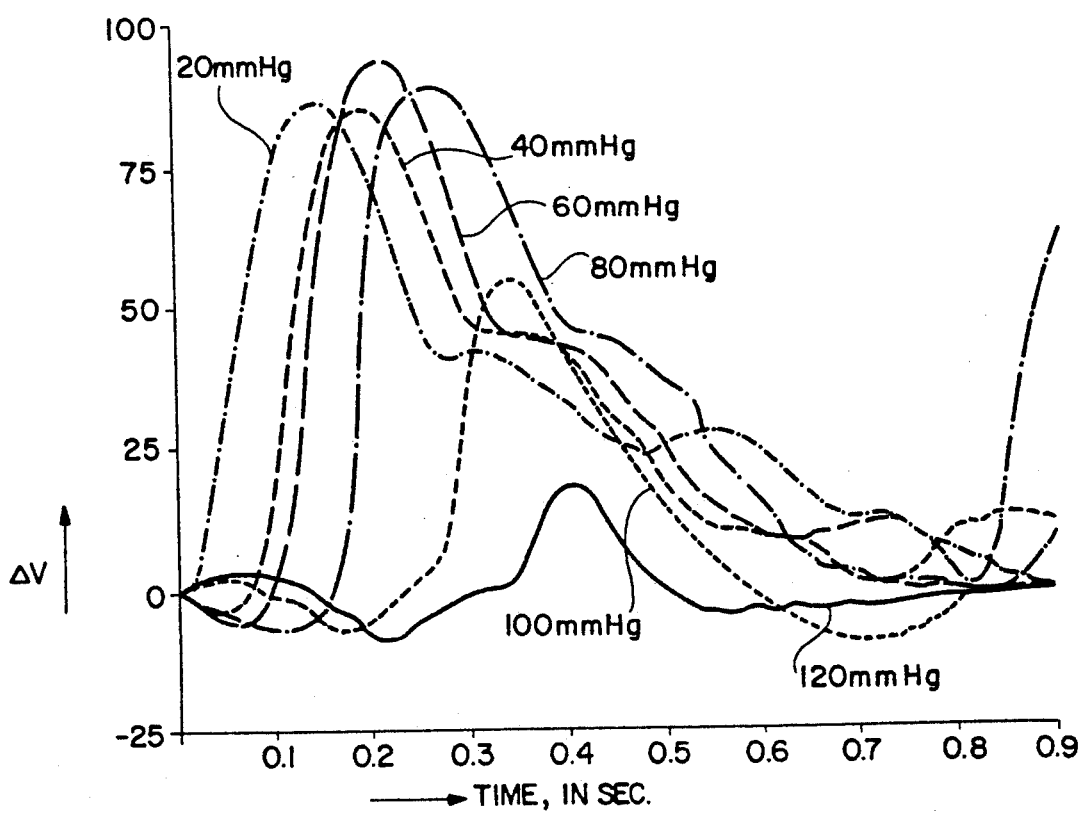

FIG. 22 illustrates volume pulse recordings from a limb segment distal to a pressure cuff, at different cuff pressures in the pressure cuff. The signal was averaged and overlapped as per FIG. 21.

Figure 23:
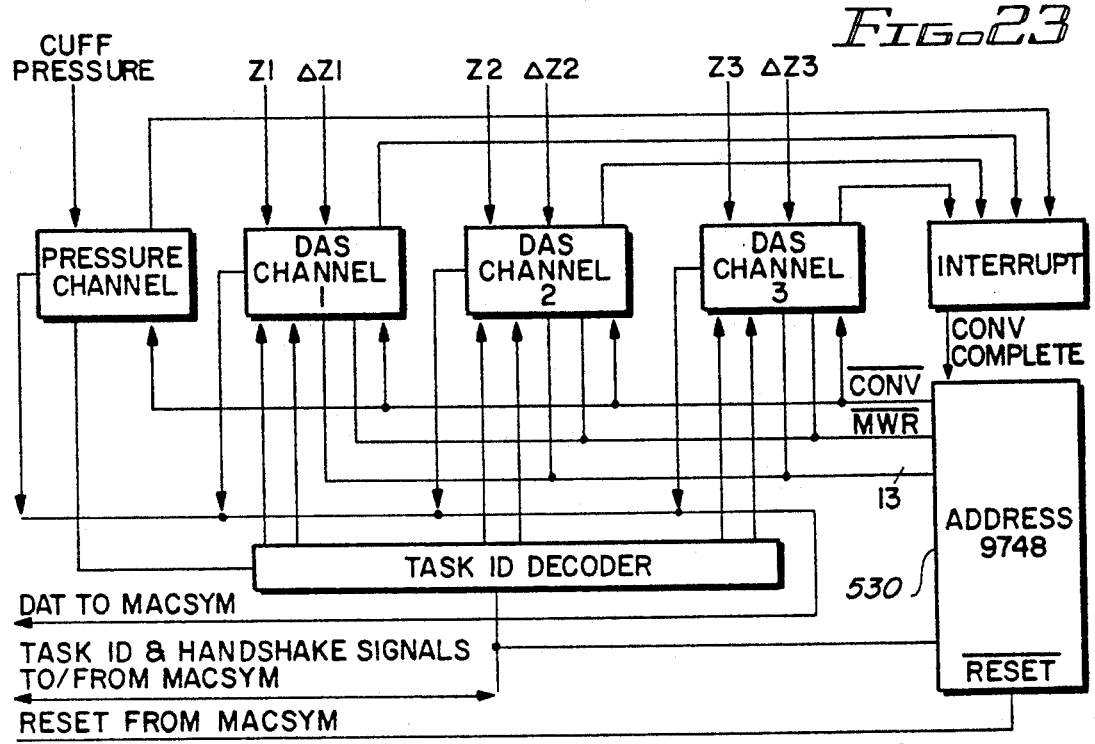

FIG. 23 illustrates a data acquisition and storage (DAS) unit as a block diagram.

Figure 24:
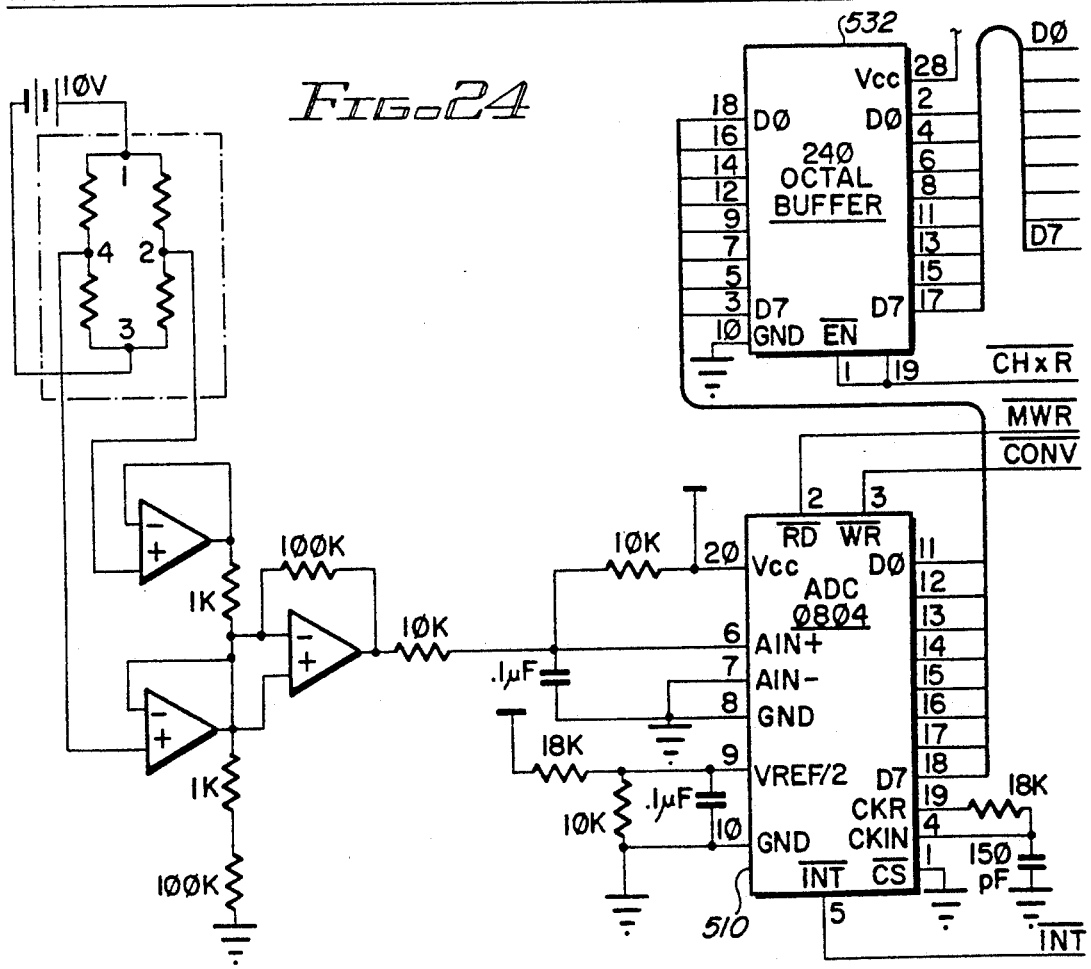

FIG. 24 illustrates the pressure channel as a schematic diagram.

Figure 25:
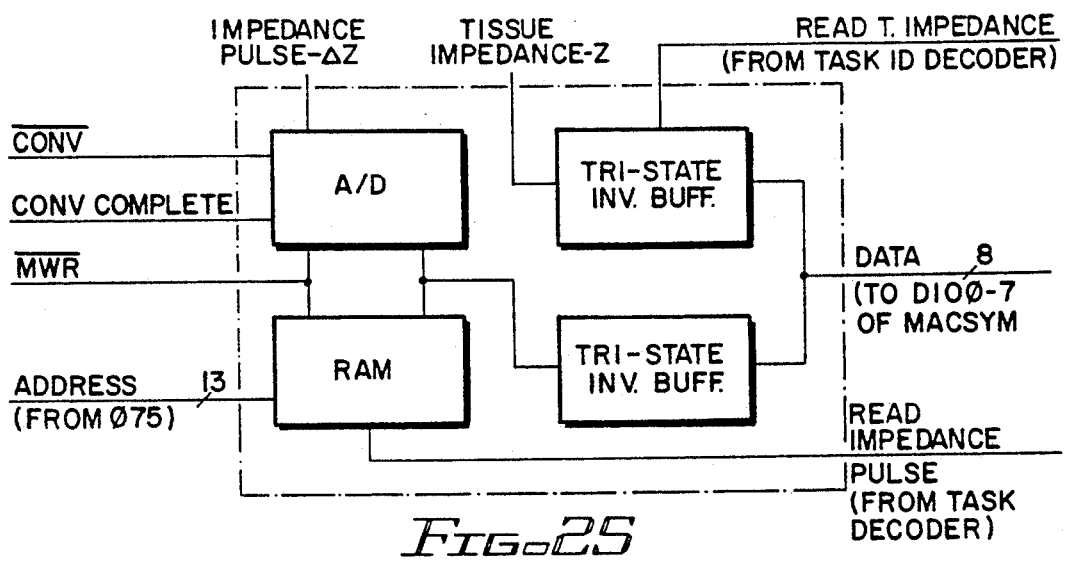

FIG. 25 illustrates a data acquisition and storage channel of the DAS as a block diagram.

Figure 26:
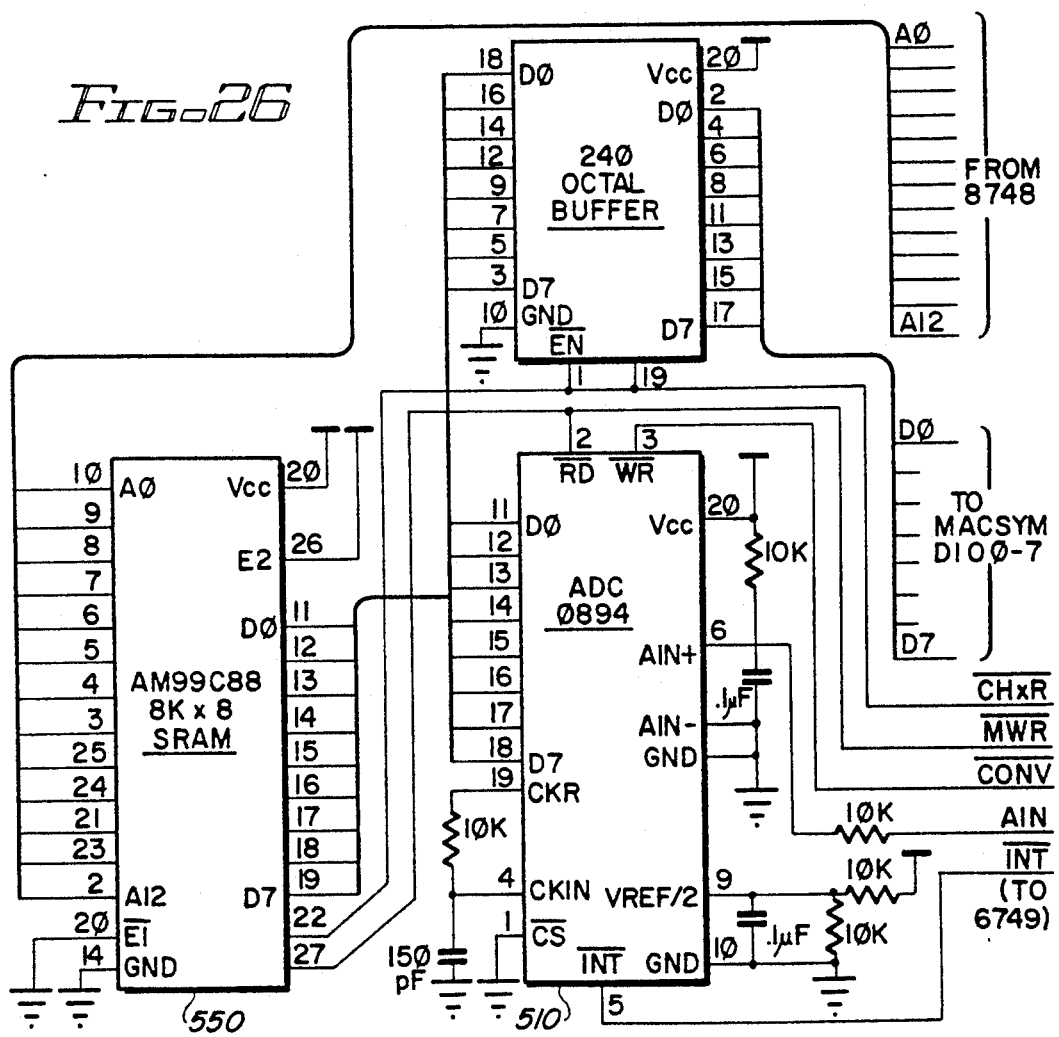

FIG. 26 illustrates a data acquisition and storage channel of the DAS as a schematic diagram.

Figure 27:
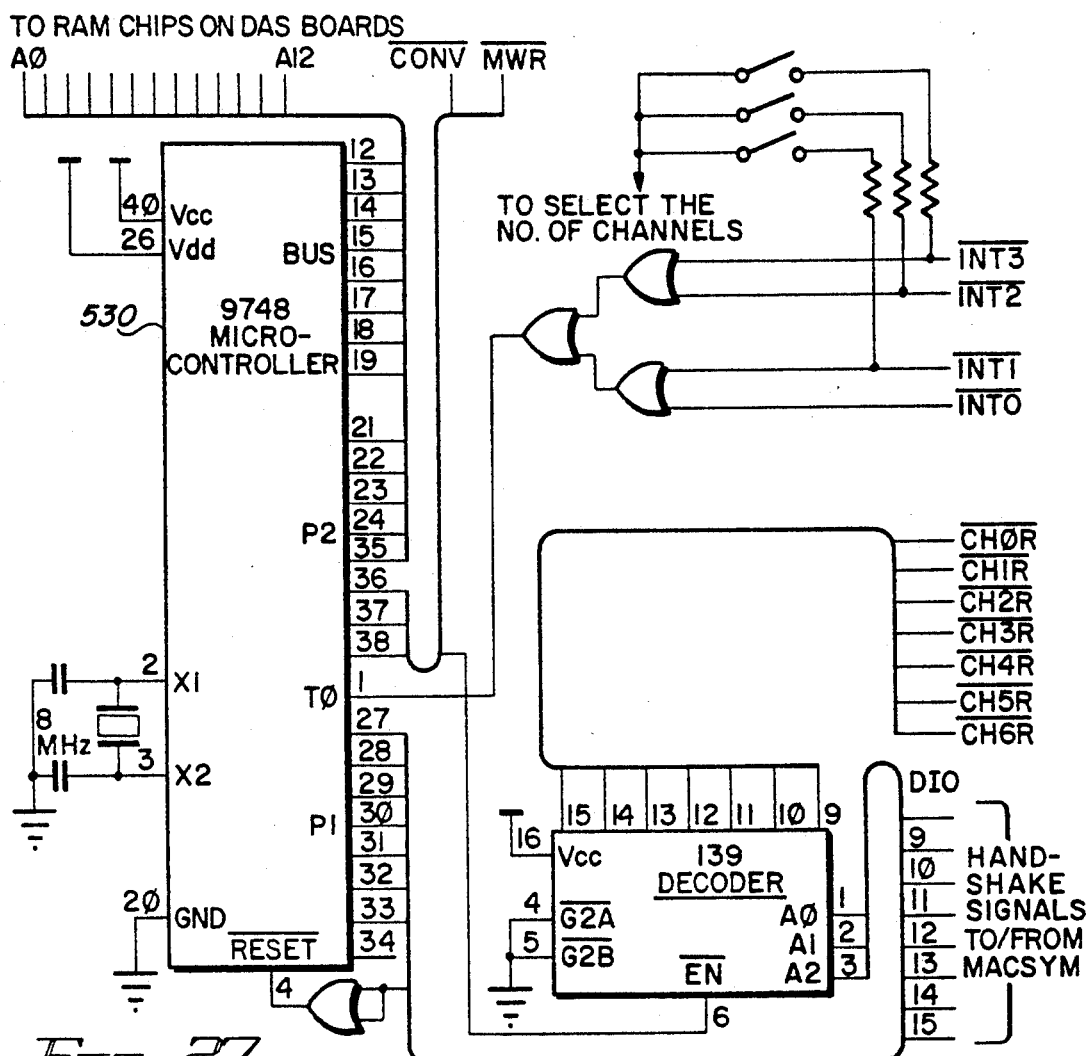

FIG. 27 illustrates the controller for the DAS channels and the pressure channel.

Figure 28:
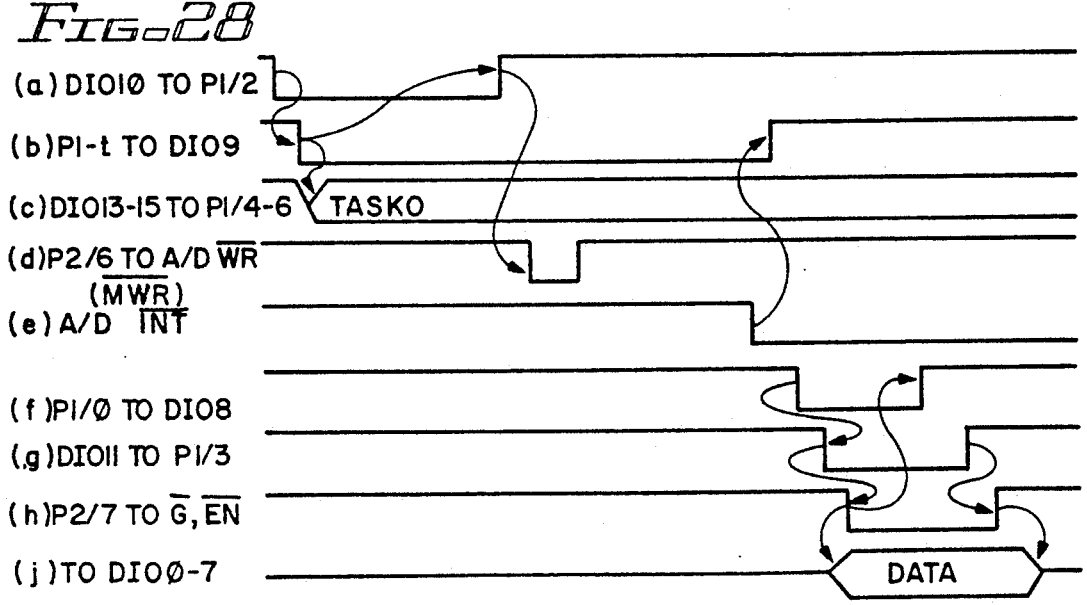

FIG. 28 illustrates a typical handshaking sequence as a timing diagram for signals (a) through (i).

Figure 31:
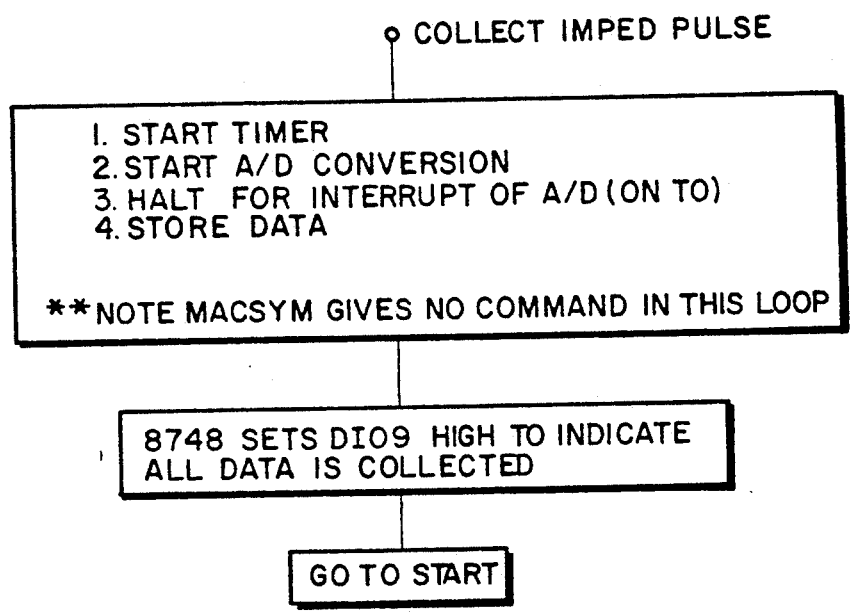

FIGS. 29, 30 and 31 illustrate a typical handshaking sequence as flow charts.

Figure 32:
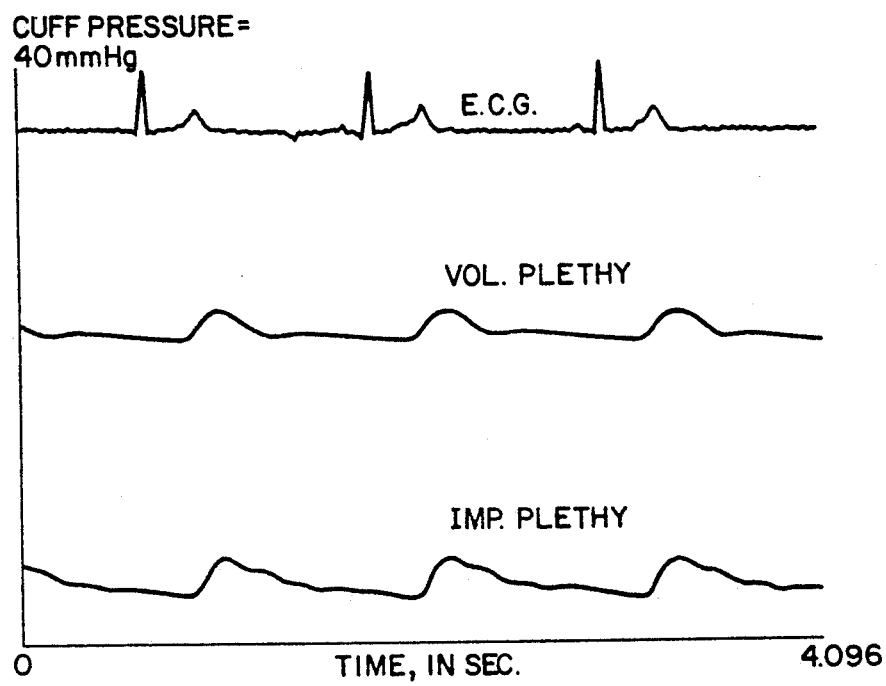
Figure 33:
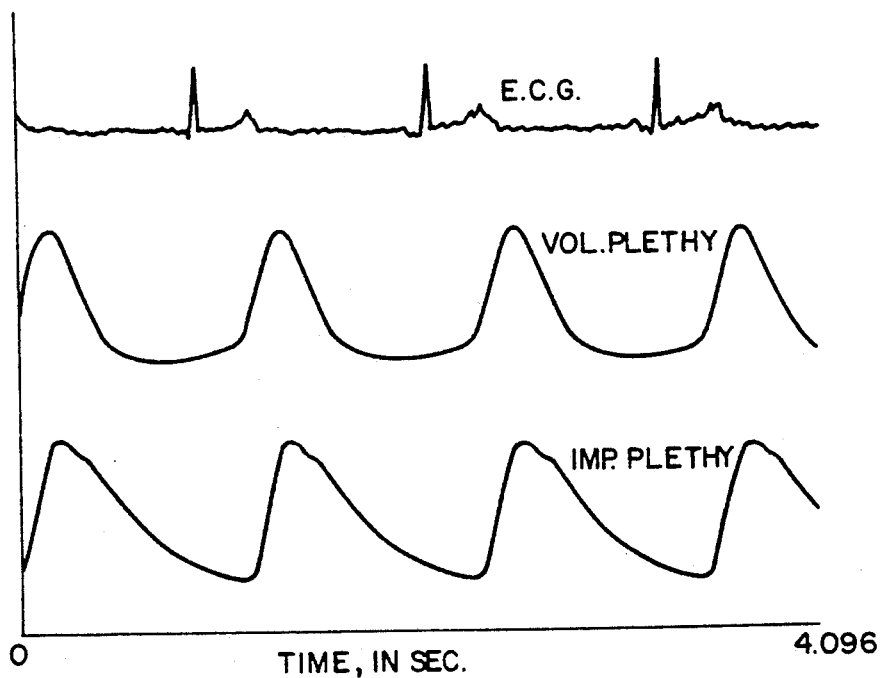

FIGS. 32 and 33 respectively illustrate simultaneous recordings of three physiological signals, that is, ECG, volume and impedance plethysmographic signals from under a pressure cuff, on the lower leg at a cuff pressure of 40 mm Hg (FIG. 32) and at a cuff pressure of 80 mm Hg (FIG. 33).

DETAILED DESCRIPTION OF THE PREFERRED EMBODIMENTS

The present invention, in general, relates to a method and a system for detecting the onset of atherosclerosis and further for detecting the degree of atherosclerosis by non-invasively sensing certain physical parameters of a human artery. Since it is difficult, if not impossible, to ascertain the degree of occlusion in a human artery at various stages and in various diseased conditions, the present invention draws on data collected during a scientific study of 15 males cynomolgus (*Macaca fascicularis*) monkeys (herein "the monkey study"). The monkey study correlations are linked to a human study that is discussed separately. A detailed description of a volume plethysmograph system and an electrical impedance plethysmograph system is also provided herein.

The Monkey Study

The male monkeys were fed a control diet (n=3) or a high cholesterol diet (n=12) for 26 months. The control diet contained 0.16 mg of cholesterol/cal., while the high cholesterol (or test) diet contained 1.0 mg of cholesterol/cal., and both diets had 40% of calories from butter. During the 26 month test period, cholesterol concentration and blood pressure data were monitored quarterly.

Prior to sacrificial death of the monkeys, non-invasive measurements were performed and non-invasive arterial data gathered on the left and right legs of the monkeys using electrical impedance plethysmography and volume plethysmography, respectively.

The method used non-invasive plethysmography for determination of arterial volume change, ΔV, from a limb segment. This arterial volume change is included in the term arterial blood volume differential used herein. Arterial compliance C was determined as a ratio of ΔV to the blood pressure differential or pulse pressure ΔP. To obtain the compliance value of the artery C at different arterial transmural pressures, a pressure cuff was wrapped around the upper leg and cuff pressure was incrementally increased. Transmural pressures refer to the pressures across the artery wall. At zero transmural pressure, the internal systemic pressure in the artery equals the external pressure applied on the arterial wall via the pressure cuff. When the external cuff pressure is slightly higher than diastolic pressure, the transmural pressure was near zero and the maximal arterial volume change ΔV was recorded. The maximal ratio of ΔV and ΔP, that is, the maximal ratio of arterial blood volume change and pressure differential is the peak compliance value $C_p$ for the artery under study.

After initial anesthetization with 1.2 ml ketamine, each monkey was shaved on both sides of the upper thigh and lower leg to facilitate good contact of the electrodes and pressure cuffs. In the experiment, we obtained Pedisphyg cuffs from Axon Medical Systems of Branford, Conn. that were 6×18 cm (width by length), and 7×21 cm, or 9×25 cm. A four electrode, 100 kHz, 8 mA automatic resetting electrical impedance plethysmograph (ZPG) originally designed by Shankar and Webster, was used in the monkey study. See T. M. R. Shankar and J. G. Webster, "Design of an Automatically Resetting Electrical Impedance Plethysmograph," *J. Clin. Eng.*, Vol. 9, p. 129 (1984). This instrument is easy to use and has signal processing circuits which reduce the noise to a low noise value and correct the drift in the signal by a resetting mechanism to achieve a very high sensitivity. Also, the electrical impedance plethysmograph made in accordance with Shankar and Webster article is adapted to record extremely small amplitude signals. The impedance signals are about 0.01% to 0.1% of the carrier signal. The carrier signal is directly proportional to the tissue impedance (about 20–40 ohm). Referring to FIG. 7b, the noise is seen to be less than 0.15 microliters/cm, while the signal ranged from about 0.8 to 14 microliters/cm. This, for the instrument, corresponds to a signal range of 0.04 to 0.4% amplitude modulation, while the noise was of the order of 0.008% amplitude modulation. This may be compared to typical amplitude modulation signals of 50% or more used in AM broadcasts. Two 2.5 mm wide aluminum electrodes (No. 425, 3M Company, St. Paul, Minn.) were fixed 1.8 cm from the mid-line of a 7 cm Pedisphyg cuff, which was strapped around the shaved upper thigh of the monkey. The electrodes were used as voltage electrodes V1 and V2 for the ZPG. Five (5) mm wide paste-coated tape electrodes (3M brand electrode tape, No. M60001) served as current electrodes I1 and I2 for the ZPG and were placed on the left and right lower leg 2 cm from the respective ankle joints. Impedance pulse and tissue impedance were reported from the upper thigh by connecting leads I1, V1, V2, and I2 to the impedance plethysmograph.

Segmental volume plethysmographic recordings were made with a volume plethysmograph (Vasograph model 186, Electro-Diagnostic Instruments, Burbank, Calif.) which was adapted for use with a 6/7 cm wide Pedisphyg cuff. Arteriosonde model 1020/1022 ultrasonic blood pressure instrument (Kontron Medical Instruments, Evert, Mass.) was used to measure blood pressure at the left leg/left arm. Kontron's Gelisonde II was used to couple the ultrasonic transducer to the limb.

The anesthetized animal was placed on the left side and a blood pressure measurement was made on the left leg. In the event that no pulse could be obtained from the leg, blood pressure was recorded from the left arm. The Arteriosonde cuff was removed and the 7 cm Pedisphyg cuff with glued voltage electrodes V1 and V2 was wrapped around the upper left thigh, while the current electrodes were placed as described above. Connections were made to the impedance plethysmograph (ZPG) for impedance pulse measurement from the left upper thigh. The cuff was then inflated to suprasystolic pressure and allowed to deflate at approximately 3 mm Hg/sec. This procedure was repeated seven times in order to relax the arterial smooth muscles. In an earlier study on human subjects it was demonstrated that this step reduced day to-day variability in the measurement.

The electrical impedance plethysmograph had a sensitivity of 66 mV/milliohm and an output noise of 0.33 milliohm p-p, while the impedance pulsations were typically 5–500 milliohm. Tissue impedance is about 20–40 ohms.

Tissue impedance Z and impedance pulsations were recorded at increasing cuff pressure increments of 10 mm Hg. At each increment, the pressure was held for 20 seconds to reduce hysterisis. After recorder adjustment for proper recording of the signal, the impedance pulse was recorded for 5 seconds. The cuff was deflated between pressure increments. This was continued until the artery was completely collapsed as indicated by an absent impedance pulse. The signals at each incremental induced pressure level were averaged to reduce the effect of breathing. The following equation was used to determine the arterial volume change:

$$\Delta V = [p_b L^2 \Delta Z]/Z^2 \qquad \text{Eq. 1}$$

where $P_b$=blood resistivity (1605 L·cm), L=3.5 cm, ΔZ=amplitude of the impedance pulse in milliohn, and Z=tissue impedance of the limb segment in ohn.

Figure 7A:
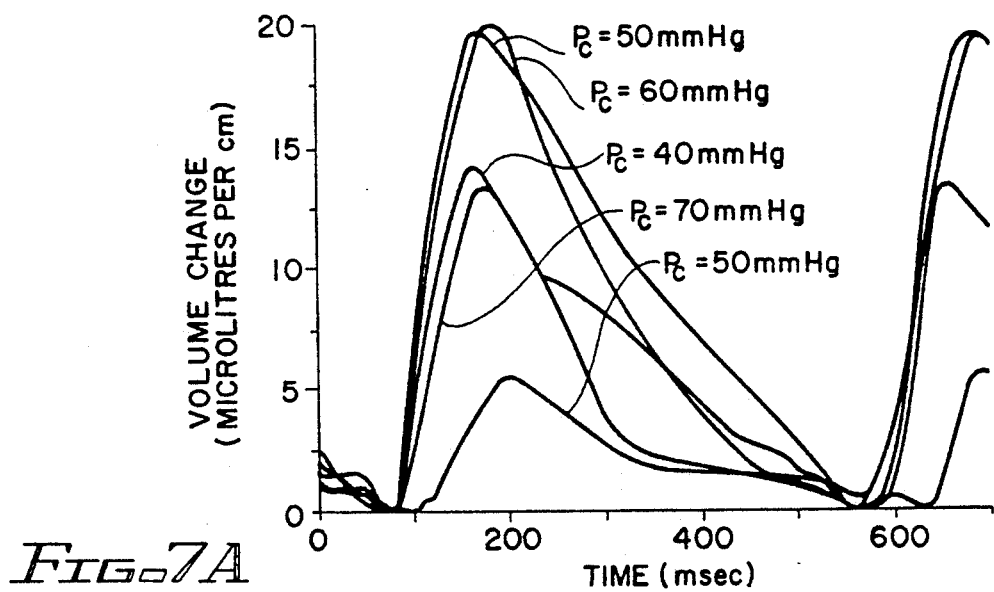
FIGS. 7a and 7b illustrate volume pulse recordings at different levels of cuff pressure.
Figure 7B:
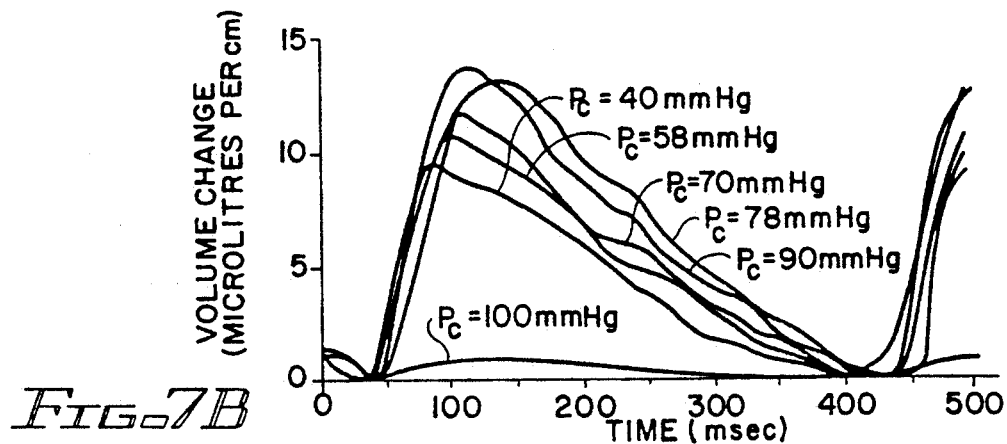

FIGS. 7a and 7b illustrate volume pulse recordings at different levels of pressure. FIG. 7a represents data from one monkey and FIG. 7b represents data from a different monkey having a higher degree of atherosclerosis (determined after sacrifice).

The Pedisphyg cuff was then removed from the upper left leg and another blood pressure measurement was made with the Arteriosonde. Recordings were then made on the right upper thigh with the volume plethysmograph at variable cuff pressures (10 mm Hg increments) until no discernible pulse was recorded. The signals were calibrated for every run with the aid of a standard 1 ml injection of air into the cuff. The resulting signal is used to calibrate the system. Signals at lower cuff pressures, typically less than 50 mm Hg, are inaccurate because of poor transmission of the arterial pulse to the cuff through intervening tissue. See, generally, B. I. Mazhbich, "Non-Invasive Determination of Elastic Properties in Diameter of Human Limb Arteries," Pflugers ARCH, Vol. 396 (1983) p. 254. Hence, only the maximal volume change signal, typically obtained at 80 mm Hg cuff pressure, was used for analysis.

Blood pressure was determined again on the left leg of each animal. Indirect pressure was measured with the Arteriosonde on one monkey where direct data was not obtainable. The entire set of recordings including impedance plethysmography took about 30 minutes to collect. The monkey was typically given 0.2 ml ketamine between experiments to keep it anesthetized. Ketamine anesthesia does not significantly affect mean blood pressure. See M. I. Castro, J. Rose, W. Green, N. Lechner, D. Peterson and D. Taub, "Ketamine-HCl as a suitable anesthetic for endocrine, metabolic, and cardiovascular studies in *Macaca fascicularis* Monkeys," 168 Proc. Soc. Exp. Biol. Med. 389 (1981). Two monkeys had considerable involuntary movement resulting in motion artifacts. These studies were terminated prematurely if the monkey could not be restrained sufficiently to reduce the motion artifacts. The 6 and 7 cm Pedisphyg cuffs were replaced with 7 and 9 cm cuffs in experiments with two larger monkeys to ensure that the cuffs encircled the limbs completely.

An arterial catheter was inserted through the right femoral artery of each monkey and threaded into the abdominal aorta with radiological visualization. This direct blood pressure measurement was recorded and the monkey was transferred to another lab for other noninvasive studies.

Morphometric analysis was performed on bilateral common iliac, external iliac, femoral, and carotid arteries. At the time of necropsy the arterial segments were pressure perfusion-fixed in situ with 10% neutral buffered formalin at 100 mm Hg followed by perfusion with Barium gel mass. The site of the largest plaque was selected and processed for microscopy. Measurements were made of intimal area, intimal thickness, percentage of intima in arterial tissue (PIAT), and percentage damaged media. Measurements were made from projected microscopic images using a sonic digitizer interfaced with a microcomputer. See J. F. Cornhill and M. G. Bond, "Morphology: Morphometric Analysis of Pathology Specimens," in: M. G. Bond, W. Insull, Jr., S. Glagov, A. B. Chandler, J. F. Cornhill (eds) *Clinical Diagnosis of Atherosclerosis, Quantitative Methods of Evaluation*, Springer-Verlag, New York, 1983, p. 67.

Monkey Study Statistics

The two monkey groups (control and high cholesterol diet groups) were compared using two-sample t-tests. Tests were performed for peak compliance, the mean PIAT of corresponding iliac arteries (common and external), the carotid arteries, and mean PIAT of both the arterial beds, total plasma cholesterol and $\alpha$-cholesterol concentration, and direct blood pressure. Pearson product moment correlation coefficients were determined between the pathology measures and other parameters listed above that are used for predicting the degree of atherosclerosis. Multiple linear regression was used to determine the combination of these parameters that yielded a best fit with significant regression coefficients. See T. J. Boardman, "Statistical Library for HP Series 200 Computers," Hewlett-Packard Desktop Computer Division, Ft. Collins, Tex., 1982.

Monkey Study Results

Table 1 shows body weight, total plasma cholesterol (TPC) and $\alpha$-cholesterol concentrations, and direct systolic and diastolic blood pressures (SYST-BP and DIAS-BP, respectively) for the two groups.

TABLE 1

| Group (No.) | Total plasma cholesterol TPC (mg/dl) | $\alpha$-Cholesterol (mg/dl) | Direct systolic pressure SYST-BP (mm Hg) | Direct diastolic pressure DIAS-BP (mm Hg) | Body weight (kg) |
|---|---|---|---|---|---|
| 1. (n = 5)* | 342 ± 127** | 47 ± 21** | 114 ± 13 | 74 ± 14 | 3.95 ± 0.16 |
| 2. (n = 22) | 719 ± 118 | 24 ± 6 | 134 ± 28 | 83 ± 14 | 4.42 ± 0.57 |

*n = number of limbs examined.
**The 2 groups were significantly different (P <0.01).

Bilateral noninvasive plethysmographic recordings and morphometric vascular measurements on both lower extremities as well as the carotid arteries were made on most animals.

With respect to the morphometric data obtained postmortem, only the values of the parameter "percentage of Intima in Arterial Tissue" (PIAT) for the common iliac, external iliac, femoral, and carotid arteries were utilized in this study. This parameter has been identified by other researchers as a valuable or significant indicator of atherosclerotic disease. See J. K. Sawyer, "A Comparative Quantitative Study of Atherosclerosis in Abdominal, Aorta, Coronary, and Carotid Arteries of Hypercholesterolemic *Macaca fascicularis.*" supra.

Table 2 lists the femoral artery peak compliance (PK-CMPL), and PIAT values for the corresponding iliac arterial bed (ILIAC-PIAT) (average of PIAT of external and common iliac arteries) and femoral arteries (FEM-PIAT), carotid arteries (CRTD-PIAT), and the average for iliac and carotid arterial beds (MAJOR-PIAT). Since FEM-PIAT data were either missing or zero for many monkeys, to obtain more meaningful data, MAJOR-PIAT was obtained by averaging only the data from external and common iliac arteries (at least one of these two) and carotid arteries. For all but one monkey the directly measured blood pressure was used in the determination of the compliance values. This directly measured blood pressure was the invasively obtained as explained earlier.

Morphometric analysis on both sides of peripheral arterial systems was conducted so that this data could be correlated with corresponding noninvasive plethysmographic records on the left and right thighs. Advantages of impedance plethysmography (ZPG) are ease of calibration and high signal-to-noise ration as compared to volume plethysmography (VPG). In addition, VPG required a cuffed pressure of at least 50 mm Hg for adequate recordings. However, both ZPG and VPG may be used interchangeably to record maximum arterial volume change.

TABLE 2

| Group (No.) | Peak compliance: PK-CMPL nl × mm Hg$^{-1}$ × cm$^{-1}$ | % Intima in arterial tissue (iliac): ILIAC-PIAT | % Intima in arterial tissue (femoral): FEM-PIAT | % Intima in arterial tissue (carotid): CRTD-PIAT | % Intima in arterial tissue (iliac and carotid): MAJOR-PIAT |
|---|---|---|---|---|---|
| 1. (n = 5)* | 444 ± 54** | 12 ± 10** | 0 ± 0 | 24 ± 12** | 14 ± 9** |
| 2. (n = 22) | 292 ± 132 | 47 ± 16 | 17 ± 29 | 50 ± 15 | 49 ± 15 |

*n = number of limbs examined (FEM-PIAT is based on data from fewer limbs).
**The 2 groups were significantly different ($P < 0.01$).

The graphs of FIGS. 8a, b, c and d plot the measured arterial volume change (for example, the blood volume differential through the artery) against the cuff pressure (for the left thighs) for four different monkeys. The cuff pressure is sometimes referred to herein as the level of induced pressure on the artery under study. The graphs represent data from animals having different amounts of atherosclerosis. Particularly, monkey 1402 (FIG. 8a) had the best arteries, that is, a low degree of atherosclerosis. Monkey 1395 (FIG. 8b) had a higher degree of atherosclerosis according to PIAT data and in comparison with monkey 1402. Monkeys 1394 and 1392 (FIGS. 8c and d) had progressively higher levels of atherosclerosis. The discovery that the waveforms change from low levels of PIAT to high levels of PIAT represents a significant advance in ascertaining the onset of atherosclerosis and in quantifying the degree of atherosclerosis in monkeys. This discovery, as discussed later, is transferable to humans. The ZPG recordings at different cuff pressures were used to reconstruct the arterial volume-pressure curves.

Two Sample T-test

Two sample t-tests for the two groups (Group 1 and 2) showed that TPC, α-cholesterol, ILIAC-PIAT, CRTD-PIAT, MAJOR-PIAT, and PK-CMPL were significantly different ($P < 0.01$), but not SYST-BP and DIAS-BP ($P < 0.10$). FEM-PIAT has not been analyzed because of insufficient data points.

Correlation coefficients

The data from both groups were pooled for this purpose. The Pearson correlation coefficient for association between ILIAC-PIAT and PK-CMPL (peak compliance) was $-0.39$ ($P < 0.10$, $n = 21$). The corresponding values for association of ILIAC-PIAT with TPC, α-cholesterol [the quantity α-cholesterol in animals is generally equivalent to human HDL cholesterol], SYST-BP and DIAS-BP were 0.49 ($P < 0.05$), $-0.36$ ($P = 0.10$), 0.44 ($P = 0.05$), and 0.30 ($P > 0.10$) respectively. The correlation coefficients for association of PK-CMPL with certain other physiological parameters were $-0.80$ ($P < 0.001$) with SYST-BP, $-0.71$ ($P < 0.001$) with DIAS-BP, and not significantly different from zero with TPC and α-cholesterol concentration.

The Pearson correlation coefficient was obtained to determine the correlation between the peak compliance in the thigh and the MAJOR-PIAT. This correlation had a value of $-0.52$ ($P < 0.01$, $n = 27$). The corresponding values for association of MAJOR-PIAT with TPC, α-cholesterol, SYST-BP and DIAS-BP were 0.69 ($P < 0.001$), $-0.60$ ($P < 0.001$), 0.55 ($P < 0.01$) and 0.48 ($P < 0.01$) respectively.

Multiple Linear Regression

Using multiple linear regression, the best fit for ILIAC-PIAT in terms of various combinations of the parameters was determined: PK-CMPL, TPC, α-cholesterol, SYST-BP, and DIAS-BP. The best regression fit with significant coefficients was obtained with PK-CMPL and α-cholesterol concentration as independent parameters. The corresponding F values were significant at $P = 0.05$. The constant was 94.5 with the regression coefficients for PK-CMPL and α-cholesterol of $-0.066$ and $-1.25$, respectively. All three were significant at $P < 0.05$. The corresponding correlation coefficient was $-0.58$.

Multiple linear regression was also used to determine the best fit for MAJOR-PIAT with various physiological parameters monitored as independent variables. The best regression fit was again obtained with PK-CMPL and α-cholesterol concentration. The corresponding F values were significant at $P < 0.005$. The constant was 84.4 with the regression coefficients for PK-CMPL and α-cholesterol concentration of $-0.062$ and $-0.77$, respectively. All three were significant at $P = 0.01$. The corresponding correlation coefficient was $-0.73$.

Comparison of Peak Compliance Values on the Opposite Limbs

The peak compliance determined on the left and right legs, with a ZPG and VPG, respectively, were within a few percent of each other, for some of the monkeys. There were two monkeys with values that differed by a factor of two. The vasculature and degree of atherosclerosis may not be uniform bilaterally resulting in this discrepancy. Morphometric data were not available for both sides in these monkeys.

Pathologic Validation

Arterial compliance can be determined from:

$$C = (2.16\ V)/[E_t(h/r) - 1.26\ P] \qquad \text{Eq. 2}$$

where C=compliance, V=internal volume, $E_t$=tangential Young's modulus, h=thickness of the wall, r=internal radius, and P=transmural pressure. The above equation is provided only for a qualitative discussion and may have to be modified for arteries with moderate to advanced atherosclerosis. The atherosclerotic disease process consists of three interrelated phenomena: (1) intimal smooth muscle cell proliferation; (2) deposition of intra and intercellular lipids, and (3) formation of large amounts of fibrous and connective tissue, mainly collagen, by the proliferated smooth muscle. The causal relationship of these changes is at present controversial, however intimal lesions are a prominent and rapid response to hypercholesteremia in nonhuman primate models. In human atherosclerosis, a modified arterial medial smooth muscle cell (MSMC) is usually by far the most prevalent cellular component in the raised atherosclerotic plaque.

Increased collagen content may not directly increase $E_t$, since accumulated collagen is highly fragmented, but its presence may increase stiffness. Both smooth muscle cell proliferation and collagen formation tend to increase h and decrease r. The above equation Eq. 2 predicts that compliance (C) decreases with atherosclerosis. Compliance also appears to be the mechanical parameter that changes most with progressing atherosclerosis. In the experiments, peak compliance was measured near zero transmural pressure where the ratio of h/r is the highest. Therefore, peak compliance provides an indirect indication of atherosclerosis. The other parameter that has been studied, pulse wave velocity is inversely proportional to the square root of compliance and is a less sensitive method for use at a specific site but conceivably is useful as descriptor of global atherosclerosis.

The experimental data, in agreement with the above predictions, demonstrate a decrease in peak compliance with increasing intimal tissue of arteries. Correlation coefficients may not have been higher since the morphometric measurements were made from samples of only the most significant lesion present in each arterial segment, and hence do not represent average morphometric measures, but rather the worst case values.

Anomalies

Comparison of the peak compliance data with quantitative pathology data from peripheral arteries (Table 2) shows that there is a tendency for lower peak compliance values to be associated with a higher PIAT and vice versa. However, an anomaly exists with regard to one monkey in group 2 which had a high PIAT measure but with good peak compliance value. The physiological compliance of the left lower leg was also seen to be normal for the monkey. The reason for this is not clear at present.

When one monkey with this anomaly was excluded, the correlation of ILIAC-PIAT with PK-CMPL changed to $-0.59$ ($P<0.01$, $n=19$) from $-0.39$ ($P<0.05$, $n=21$). The corresponding correlation coefficient of ILIAC-PIAT with TPC remained about the same.

The Human Correlation

The present invention relates to a method of detecting the onset of atherosclerosis, the method of detecting or quantifying the degree of atherosclerosis and several systems for carrying out that method.

FIG. 1 diagrammatically illustrates arterial occlusion versus the time or atherosclerotic disease progression. When the artery is fully occluded, that is, at 100%, there is no blood flow through the artery. An ECG stress test can be utilized to determine when the occlusion reaches approximately 70% as noted in FIG. 1 at point A. An angiogram can be conducted on the human patient to determine whether the occlusion has reached 50% (Point B). However, the angiogram is an invasive procedure which utilizes electronic image processing. In contrast to these tests, the method in accordance with the present invention can detect occlusion or stenosis of an artery at approximately 20% or point C in FIG. 1. Further, the present invention detects not only the onset of atherosclerosis but also can ascertain the degree of atherosclerosis. In contrast to the present invention, high resolution, B-mode ultrasound is able to detect 15 to 50% stenosis. See M. G. Bond, S. K. Wilmoth, G. L. Enevold and H. L. Strickland, "Detection and Monitoring of Asymptomatic Atherosclerosis in Clinical Trials," The American Journal of Medicine, Vol. 86, Suppl. 4A, Apr. 17, 1989, pp. 33-36. The method has a replication maximum variation of 0.2 mm in arterial wall thickness—common carotid artery has a normal thickness of 0.6 mm, which according to the cited reference increases approximately 0.33 mm/year, with atherosclerosis progression. However, for 75 to 100% stenosis B-mode ultrasound imaging may severely form shadowing. Sensitivity for the range of 50 to 75% stenosis is not known. One should, however, note that B-mode ultrasound method needs a skilled operator (asonographer), proper positioning of the transducer, and interpretation by a trained medical doctor. The method thus is a time consuming and expensive method that can only be performed in a hospital with specialized equipment and personnel. The method in accordance with the principals of the present invention on the other hand, is safe, simple, and inexpensive, in addition to being non-invasive evaluation over the entire range of stenosis, and for evaluation of progression/regression in the same individual, with change in risk factors. The B-mode ultrasound procedure cannot currently be used to detect the degree of atherosclerosis due to this poor degree of sensitivity.

There are two types of systems that can be used in conjunction with the present invention. One system includes an electrical impedance plethysmograph, shown generally in FIG. 2 and FIG. 14, and the other includes a volume plethysmograph, generally shown in FIG. 9.

FIG. 2 schematically illustrates an electrical impedance plethysmograph (ZPG) coupled to the legs of a human. This ZPG was used to obtain the human data which is correlated with the monkey study data herein. Impedance plethysmograph 10 is a 100 khz, 8 mA automatic resetting electrical impedance plethysmograph similar to that used in the monkey study described above. The instrument has a sensitivity of 66 mV/milliohm and an output noise of 0.33 milliohm p-p, while the impedance pulsations were typically in the 5-50 milliohm range Paste coated aluminum tape electrodes (3M brand electrotape, No. M60001) were placed 4 cm proximal to both ankle joints on the human legs. Specifically, electrode 12 was placed on human leg 14 and electrode 16 was placed on human leg 18. The voltage electrodes were glued 6.2 cm apart in the middle of the pressure cuff and the cuff was wrapped around the thickest part of lower leg 18. With the human subject supine, tissue impedance Z (a representative signal) and impedance pulse $\Delta Z$ (a representative signal) were recorded by impedance plethysmograph 10. Most importantly, the tissue impedance Z and impedance pulse $\Delta Z$ were recorded at increasing cuff pressure increments of 10 mm Hg. At each cuff pressure incremental level, the pressure was held for about 20 seconds to reduce the hysterisis effect. The human subject held his/her breath for 5-10 seconds at the end of expiration and the signal was recorded. The pressure cuff 20 was deflated between pressure increments. The recording was continued until the artery was completely collapsed as indicated by no discernible impedance pulse.

FIGS. 3a, b, c and d illustrate a typical set of arterial flow recordings at selected cuff pressures. Particularly, FIG. 3a occurs at cuff pressure $P_c$ of 20 mm Hg wherein the arterial volume change $\Delta V$ was measured at 0.420 ml. The subject had a blood pressure of 120/78 mm Hg. As shown in FIGS. 3a, b, c, and d, at low cuff pressures $P_c$, arterial compliance is low as noted by a low recorded blood volume change $\Delta V$. As cuff pressure $P_c$ is increased, the pressure across the arterial wall decreases. Arterial compliance, and hence the blood volume change ΔV, increased reaching a maximum at cuff pressure $P_c$ equal to 80 mm Hq (FIG. 3c). At higher cuff pressures (FIG. 3d), the arterial wall collapsed for part of the cycle, resulting in a lower ΔV. The 240 μl, 220 μl, 410 μl and 75 μl, respectively in FIGS. 3a, b, c and d represent the scale. The term "1 s" represents one second time scale.

Returning to the particular operation of the electrical impedance plethysmograph, the entire procedure on the human subjects took 25 minutes to complete per subject. Blood pressure was determined non-invasively in the arm with a standard blood pressure cuff three times during the experiment and averaged. Then, peak compliance $C_p$ was computed by determining the maximal ratio of the arterial volume change ΔV versus the pressure differential ΔP.

FIG. 4 diagrammatically illustrates the relationship between arterial blood volume and either transmural pressure or cuff pressure. In particular, FIG. 4 illustrates the arterial volume change ΔV versus the pressure pulse differential ΔP. The graph represents the volume versus cuff pressure curve for a human patient having a blood pressure of 110/75. A cuff pressure of 80 mm Hg results in maximal arterial volume change of 155 μl per centimeter yielding a peak compliance $C_p$ as 4.4 μl per mm Hg per cm. With respect to FIG. 4, assume that the internal arterial pressure in the artery under study is maintained at 100 mm Hg and a pressure cuff has wrapped around the artery. Then as the transmural pressure decreases (due to an increase in cuff pressure), the arterial volume will decrease along the curve. If the artery were perfused from a pulsatile pump with a 35 mm Hg pulse, the electrical impedance plethysmograph would record a pulsatile change in arterial volume. The amplitude of this pulsatile change in arterial volume would be at a maximum when the transmural pressure was near zero.

FIG. 5 is a compliance-pressure curve derived from FIG. 4. Essentially, FIG. 5 depicts the slope of the curve in FIG. 4. Peak compliance is noted at the top of the curve or point A in FIG. 5. This is relatively near zero transmural pressure.

Subject Populations

In order to ascertain whether there is a definitive relationship between the change in peak compliance of an artery and various ranges of atherosclerosis, a human study was conducted on 118 subjects. The subjects were divided into nine groups for comparison purposes. Asymptomatic subjects were recruited from a university. Some of these subjects were identified as being at cardiovascular risk, due to hypertension, heredity, or smoking. Other asymptomatic subjects were classified into the age groups of 20-24, 25-49, and 50 and above. Subjects were also recruited from the peripheral vascular disease (PVD) and hypertension clinics of a hospital. Post-MI (myocardial infarction) patients on an exercise rehabilitation program at the biodynamics lab associated with the university were also studied. Human data was also collected from the People's Republic of China providing the Asian group studied because their low incidence of atherosclerosis.

Statistical Methods

The data was analyzed with the two-sample t-test to compare $C_p$ in each pair of populations at a level of significance (LOS) of 0.05. When several such tests are made, the probability of incorrectly rejecting at least one null hypothesis will be 0.3, much larger than 0.05. To overcome this problem, multiple comparisons were performed using the Bonferroni method. S. Wallenstein, C. L. Zucker and J. L. Fleiss, "Some statistical methods useful in circulation research," (special article) *Circ. Res.*, Vol. 47, pp. 1-9, July 1980. A conservative critical value for the modified t-statistic is obtained using a significance level of (LOS)/m where m is the number of comparisons to be performed.

For the results to be meaningful, Wallenstein et al. recommend limiting such multiple comparisons to a subset of all the comparisons. A comparison of asymptomatic normal populations with populations with known risk factors and/or established disease, for overlapping age ranges and for subjects with similar builds (measured with body surface area) was made.

Furthermore, to evaluate the effects of various influencing factors, viz., age, systolic pressure, diastolic pressure, body surface area, and tissue impedance (a measure of limb volume), the correlation coefficients of these factors with the peak compliance $C_p$ was determined. The three factors with the highest correlation coefficients were then used as independent variables to fit a multiple-regression line to the pooled data on $C_p$. T. J. Boardman, *Statistical Library for HP Series 200 Computers*. Fort Collins: Hewlett-Packard Desktop Comput. Div., 1982.

Results

Table 3 below shows the result for nine different groups. The columns list age, body surface area, and $C_p$. Table 4 presents the results of statistical analysis of $C_p$, using the two-sample t-test statistic. Some comparisons are seen to be highly significant, with a level of significance (LOS) of 0.01 or less, while many others are significant at 0.05. For subjects with peripheral vascular disease (PVD), an estimate of the pulse pressure in the leg as the product of the pressure index to the arm pulse pressure was made. Pressure index is defined as the ratio of the leg systolic pressure to the arm systolic pressure. D. E. Strandness, Jr., "Flow dynamics in circulatory pathophysiology," in *Cardiovascular Flow Dynamics and Measurements*, N. H. C. Hwang and N. A. Normann, Eds. Baltimore: University Part, 1977, pp. 307-334.

TABLE 3

| | Data on Different Groups (Mean ± SD) | | | |
|---|---|---|---|---|
| | Group description (n) | Age (Years) | BSA (m²) | $C_p$ (μl mmHg⁻¹ · cm⁻¹) |
| A. | Asymptomatic subjects (9) | 21.6 ± 1.4 (20–24) | 1.92 ± 0.13 | 3.08 ± 0.61 |
| B. | Asymptomatic subjects (13) | 29.9 ± 4.6 (26–47) | 1.86 ± 0.13 | 2.87 ± 0.71 |
| C. | Subjects with risk (12) | 34.2 ± 11.8 (23–47) | 2.00 ± 0.15 | 2.41 ± 0.60 |
| D. | Exercise group (23) | 42.5 ± 12.9 (27–65) | 1.91 ± 0.13 | 3.86 ± 0.69 |
| E. | Chinese from PRC (9) | 44.9 ± 2.4 (41–49) | 1.64 ± 0.09 | 2.94 ± 0.90 |
| F. | Asymptomatic subjects (7) | 69.6 ± 9.8 (54–87) | 2.01 ± 0.16 | 1.92 ± 0.63 |
| G. | Treated hypertensives (13) | 57.7 ± 9.1 (35–70) | 2.13 ± 0.13 | 1.66 ± 0.61 |
| H. | Post-MI patients* (19) | 59.5 ± 7.7 (47–72) | 1.90 ± 0.15 | 1.80 ± 0.67 |
| I. | Patients with | 61.0 ± 5.9 | 1.96 ± 0.17 | 0.72 ± 0.32 |

TABLE 3-continued

Data on Different Groups (Mean ± SD)

| Group description (n) | Age (Years) | BSA (m²) | $C_p$ ($\mu l$ mmHg$^{-1}$ · cm$^{-1}$) |
|---|---|---|---|
| PVD (13) | (52– 71) | | |

*Post-myocardial-infarction patients on exercise program.

TABLE 4

Statistical Analysis of $C_p$ for different groups
The Two-Sample t-test Statistic is shown along with
the Corresponding Level of Significance in Parenthesis

|   | B | C | D | E | F | G | H | I |
|---|---|---|---|---|---|---|---|---|
| A | 0.705 | 2.500 | 2.949 | 0.366 | 3.739 | 5.340 | 4.820 | 11.820 |
|   | (0.244) | (0.011) | (0.003) | (0.360) | (0.001) | (0.000) | (0.000) | (0.000 |
| B | NA | 1.742 | 4.056 | 0.214 | 2.979 | 4.654 | 4.311 | 9.916 |
|   |  | (0.047) | (0.000) | (0.416) | (0.004) | (0.000) | (0.000) | (0.000) |
| C | — | NA | 6.114 | 1.637 | 1.699 | 3.084 | 2.538 | 8.822 |
|   |  |  | (0.000) | (0.059) | (0.054) | (0.003) | (0.008) | (0.000) |
| D | — | — | NA | 3.078 | 6.621 | 9.508 | 9.690 | 15.322 |
|   |  |  |  | (0.002) | (0.000) | (0.000) | (0.000) | (0.000) |
| E | — | — | — | NA | 2.577 | 4.006 | 3.767 | 8.263 |
|   |  |  |  |  | (0.011) | (0.000) | (0.000) | (0.000) |
| F | — | — | — | — | NA | 0.895 | 0.380 | 5.710 |
|   |  |  |  |  |  | (0.191) | (0.354) | (0.000) |
| G | — | — | — | — | — | NA | 0.637 | 4.848 |
|   |  |  |  |  |  |  | (0.265) | (0.000) |
| H | — | — | — | — | — | — | NA | 5.395 |
|   |  |  |  |  |  |  |  | (0.000) |

Notation:
NA = Not Applicable
— = Corresponding entry exists elsewhere in the Table.

Compliance

On the average, $C_p$ decreased with age (compare groups A, B, and F, which represent asymptomatic normal populations). Groups A and B, however, were statistically indistinguishable. Group C, asymptomatic subjects identified as being at cardiovascular risk, showed significantly lower values than groups A and B. Group D is made up of subjects who exercised regularly, and they showed a significantly higher value than groups A and B. Group E (Chinese), though older (average age 44.9 years), had values in the range of groups A and B (American males, averages under 30 years). Group G consisted of treated hypertensives and had values similar to ten year older normal subjects (group F). Similarly, group H (post-MI patients on an exercise program) had values in the range of group F (older normals). However, group I (PVD patients) had much lower values than all other groups.

Figure 6:
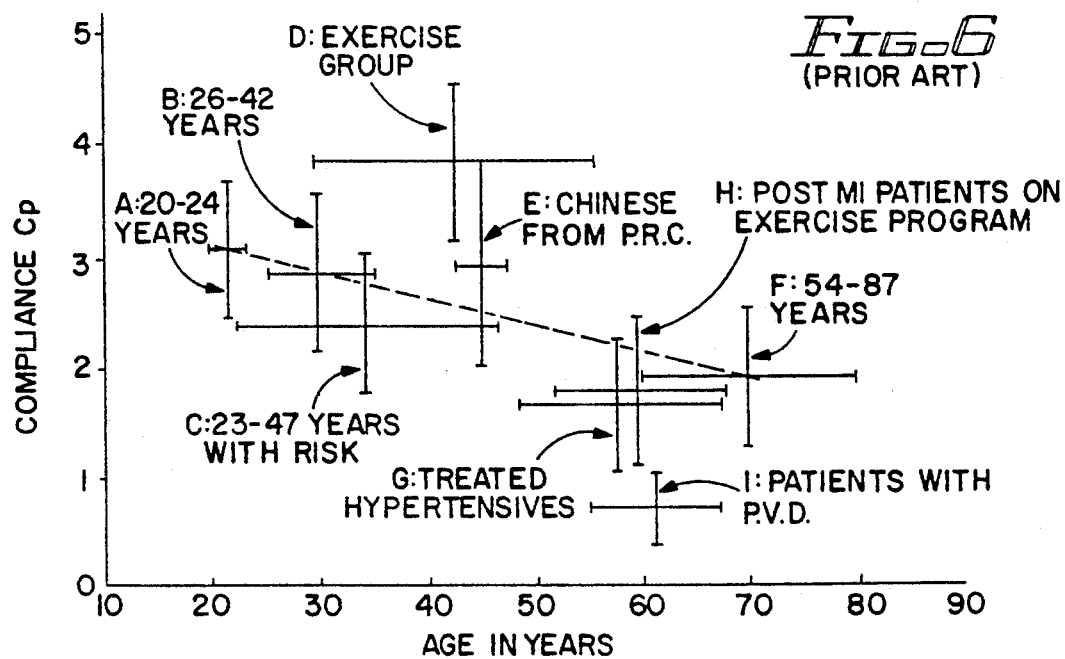
FIG. 6 plots $C_p$ versus age for human subjects.

FIG. 6 plots $C_p$ versus age. The dashed line is the regression line for groups A, B, and F. It is evident that groups D (exercise) and E (Chinese) lie above this dashed line, while groups C (subjects with risk) and I (peripheral-vascular-disease patients) lie below this line. Groups G and H lie close to the dashed line. The information in FIG. 6 parallels the statistical information presented in Table 4.

For multiple comparisons, the number of comparisons were restricted to six relevant ones: group B with groups C, D, and G; group F with groups G, H and I (see Table 3). For an individual group comparison LOS of 0.01, the multiple comparison LOS will be 0.00167, with the modified t-statistic of 3.288. See T. J. Boardman, *Statistical Library for HP Series 200 Computers.* Fort Collins: Hewlett-Packard Desktop Comput. Div., 1982. Referring to Table 4, groups C can no longer be distinguished. Groups D and G are still significantly different from the younger groups G and H, while being significantly different from group I.

Among the various influencing parameters, systolic pressure, age and tissue impedance yielded the highest correlation coefficients (0.539, 0.510, and 0.395 respectively) with $C_p$. Using multiple linear regression, the best fit was obtained with these parameters as independent variables. The regression coefficients were respectively, 0.0331, 0.0143, and 0.121, significant at 0.05.

The statistical analysis above thus indicates the following trends: (1) the peak compliance decreased significantly with increases in age, systolic pressure, and tissue impedance; (2) with regular exercise the peak compliance increased significantly above normal values, while with established PVD it deceased significantly below the normal values; (3) both treated hypertensives and post-MI patients on an exercise rehabilitation program had values similar to ten-year older normal asymptomatic subjects.

Although FIG. 6 shows a relationship between peak compliance $C_p$ and the age of a patient group, as well as showing that peak compliance decreases with certain risk factors such as hypertensive and peripheral vascular disease (PVD), this correlation was not sufficiently definitive to clearly identify the onset of atherosclerosis (when the patient may be at risk) nor to ascertain the degree of atherosclerosis in a patient. In other words, the data compiled for peak compliance and the correlation to age and blood pressure was insufficient to develop a device or a method that would be commercially acceptable to identify the onset of atherosclerosis or to quantify the extent of the disease.

In order to develop a commercially and scientifically acceptable method for detecting the degree of atherosclerosis, the monkey study was conducted. Those monkeys were grouped into a high cholesterol diet group and a control or low cholesterol diet group. The monkey study was previously described in detail. Essentially, a large amount of data was collected from an electrode impedance plethysmograph and a volume plethysmograph on the monkeys, and at the end of the study, the monkeys were sacrificed and certain arteries were analyzed to determine the extent of stenosis and, hence, the actual degree of atherosclerosis in those monkeys. The arteries were studied under a microscope and morphological data was compiled regarding the degree of stenosis. This morphological data was converted into the parameter PIAT. Statistical analysis was utilized to correlate the PIAT, the blood cholesterol for the monkeys, the blood pressure (systolic and diastolic), and the peak compliance and to determine if those factors were statistically relevant. From that analysis, a formula was developed to relate the peak compliance to the degree of atherosclerosis and to various other factors such as blood pressure, cholesterol levels, and age.

FIGS. 7a and 7b graphically show arterial blood volume change (a type of blood volume differential) at different cuff pressures $P_c$ versus time. These graphs represent data collected using the impedance plethysmograph while monitoring a parameter of the monkeys. Note that the blood volume pulse increases in amplitude from a cuff pressure of 40 mm Hg through cuff pressure 60 mm Hg. At increasingly higher cuff pressures $P_c$, blood volume pulse decreases since the artery starts collapsing (see $P_c=70$ mm Hg and $P_c=90$ mm Hg). FIG. 7a illustrates a low cholesterol monkey and FIG. 7b illustrates a high cholesterol monkey. The PIAT comparisons for these two monkeys correspond to their dietary groupings.

Figure 8B:
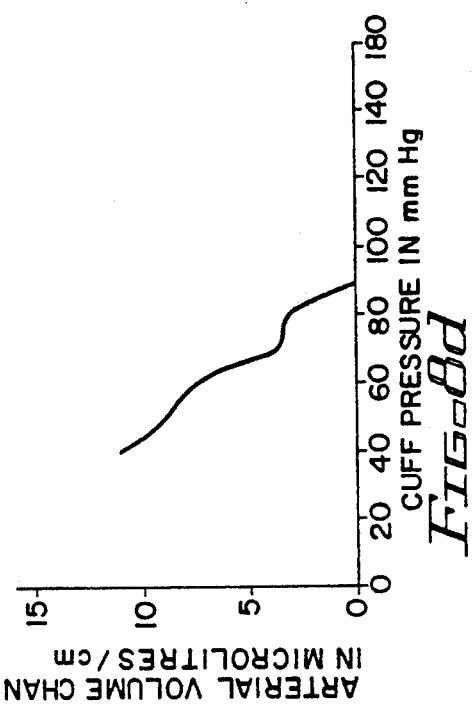
Figure 8C:
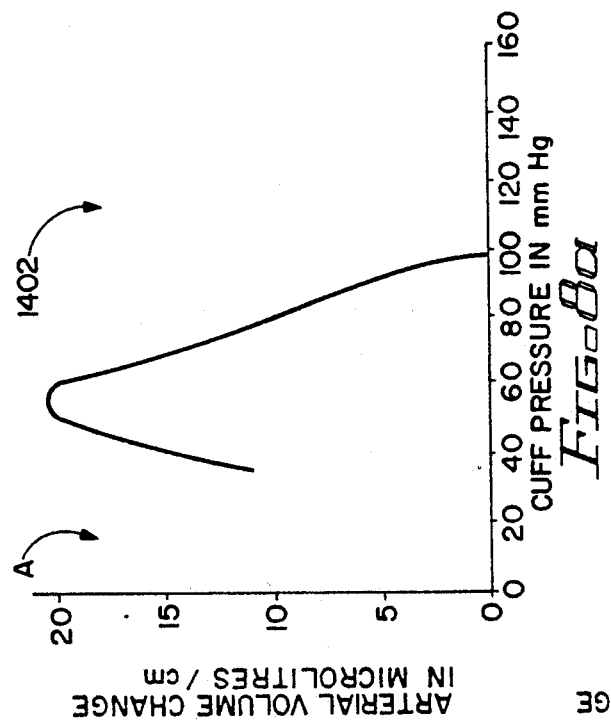
Figure 8D:
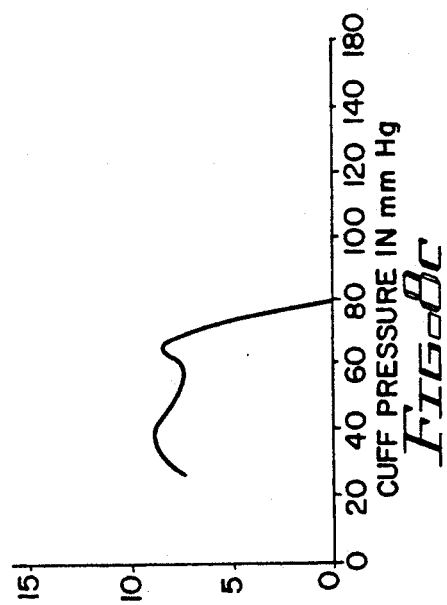

FIGS. 8a, 8b, 8c and 8d graphically illustrate arterial volume (blood volume) change $\Delta V$ versus cuff pressure $P_c$ for four monkeys. The relationship between blood volume change (a type of blood volume differential) and cuff pressure (induced pressure levels) is an indicator of the onset of atherosclerosis and the degree of atherosclerosis. Particularly, the morphological examination of monkeys 1402, 1395, 1394 and 1392 indicated that each monkey had increasingly higher degrees of atherosclerosis due to stenosis in the arteries. These graphs illustrate that the onset and degree of atherosclerosis can be ascertained by comparing the $\Delta V$ vs. $P_c$ waveforms to a plurality of predetermined waveform shapes. In particular, the onset of atherosclerosis can be detected by determining whether the sensed waveform is essentially flat, that is, determining the absence of a waveform peak as noted in FIG. 8c and 8d. Additionally, a high degree of atherosclerosis can be ascertained by determining whether the waveform is a generally linear waveform wherein the arterial volume change is inversely proportional to the induced pressure level, that is, cuff pressure. This is shown in FIG. 8d. The relationship between blood volume differential and cuff pressure is different as compared to the peak compliance The blood volume or arterial volume change is used in determining peak compliance in combination with the blood pressure differential $\Delta P$. The waveform sequence shown in FIGS. 8a through 8d does not utilize pressure differential $\Delta P$ data.

Accordingly, one method of detecting the onset of atherosclerosis includes sensing the arterial blood volume differential while the artery is placed under discrete levels of induced pressure, determining whether a function of the blood volume differential and the discrete levels of induced pressure define a waveform peak, and generating an atherosclerosis indicator signal in the absence of the waveform peak. The sensing of arterial blood volume differential can be accomplished using an electrical impedance plethysmograph shown in FIG. 2 or the volume plethysmograph which is shown in FIG. 9 and discussed in detail later. In a preferred embodiment, the blood volume change (a type of differential) is the difference between a minimal blood volume and a maximal blood volume at the respective discrete level of induced pressure. FIGS. 7a and 7b show a time base system comparing blood volume change versus time.

As discussed in detail hereinafter, the signal obtained by the electrical impedance plethysmograph or the volume plethysmograph may include various artifacts or signal distortions introduced by, for example, movement of the patient. In order to compensate for these artifacts, a number of blood volume change signals are obtained at each discrete level of induced pressure and those multiple signals at the discrete level are averaged. The averaging of the signals should be timed such that the signal portions can overlap at a certain point in the cycle with respect to the pulsatile flow through the artery. The timing aspect of the present invention will be discussed in detail hereinafter. The timing signal can be a sensed ECG or may be internally generated based upon comparing multiple signal portions of the cycle to like portions in another cycle.

In a preferred embodiment, the predetermined function of arterial volume or blood volume change versus induced pressure level is a proportional relationship, that is, it is a one to one relationship as shown in FIGS. 8a through 8d.

The degree of atherosclerosis can be ascertained by determining whether the sensed blood volume change versus cuff pressure curve matches or correlates to one of a plurality of known waveforms. For example, the known waveforms could approximate the curve show in FIGS. 8a, 8b, 8c and 8d. FIG. 8a depicts a well defined, steeply rising leading edge and steeply falling following edge curve. In contrast, FIG. 8b illustrates a slow rising lead and a steeply falling following edge curve. In further contrast, FIG. 8c depicts a curve that is essentially flat or peakless accompanied by a steep declining slope. In greater contrast, FIG. 8d shows a curve that is inversely proportional, that is, at rising cuff pressures, the blood volume change continuously falls. To ascertain the degree of atherosclerosis in a human, the arterial blood volume differential or arterial volume change would be sensed, and the volume change/cuff pressure curve derived from the patient data could be matched or correlated with one of the four curves shown in FIGS. 8a through 8d. Sensed volume change/cuff pressure curves generally matching or correlating to the curves in FIGS. 8a and 8b may be classified as "not indicating" a significant amount of atherosclerosis In contrast, if the curve obtained from the patient under study was peakless as in FIG. 8c, the present method would indicate the onset of atherosclerosis. In further contrast, if the curve was inversely proportional, a significant degree of atherosclerosis would be indicated for the patient.

The waveform can also be classified by using mathematical equations. Some parameters to classify the waveforms are (a) the ratio of arterial volume change at the peak to that of physiological pressures (cuff pressures of 20 to 40 mm Hg), (b) the three DB width along the horizontal axis, and (c) the area under the curve.

FIG. 9 is a block diagram illustrating a volume plethysmograph. The volume plethysmograph system includes pressure cuff 30, pressure relief valve 32, electronic pressure valve for deflation 34, and pump 36 associated with needle valve 38, all pneumatically coupled via air line 41 to pressure cuff 30. Electronic valve 40 and measurement chamber (1 ml chamber 42) are pneumatically coupled to pressure cuff 30 via air line 50. Air line 50 is also pneumatically coupled to pressure transducer 52. Transducer 52 is electronically coupled to differential amplifier 4 which, in turn, is electrically coupled to an analog to digital, 8 byte converter (ADC 56) ADC 56 enables the microprocessing system which includes microprocessor 58, random access memory (RAM) 60, read only memory (ROM) 62, and display device 64 to be coupled to an electronic bus generally designated as bus 66.

FIG. 10 is a structure diagram for the volume plethysmograph. The structure diagram shows the process of obtaining the volume pulse signal, the subject's interaction with the volume plethysmograph (top dashed box), and the output of the plethysmograph which is viewable and audible to the subject (right hand dashed box) Table 5 below lists and identifies the information and signals sent and received by the equipment and the subject.

TABLE 5

CUFF_CONTROL = INFLATE + STEP_DEFLATE + DEFLATE + CALIBRATE
PHYSIO_SIGNAL = COUNTER_PRESSURE_PULSE + CUFF_PRESSURE + CALIBRATION_PULSE
BIO_DATA = AGE + SEX
OPERATION_INTERACTION = START/RESTART + STOP
NORMAL_OP_IND = GREEN_LED + SINGLE_BEEP
ABNORMAL_OP_IND = MOTION_ARTIFACT + LOOSE_CUFF
MOTION_ARTIFACT = RED_LED_MOTION + MULTIPLE_BEEP
LOOSE_CUFF = RED_LED_LOOSE_CUFF + MULTIPLE_BEEP
EVAL_DATA CORRESPONDS TO THE BAR DISPLAY

The self-test and data acquisition and processing unit first generates a cuff control to the cuff which inflates the pressure cuff 30 to a pre-set level, then further inflates the pressure cuff by a small amount, that is, by 1 ml of air via chamber 42 and electronic valve 40. The cuff is then fully deflated and the unit is calibrated. The physiological signal from pressure cuff 30 includes a count or counter of the pressure pulse, the actual cuff pressure from pressure transducer 52 and differential amplifier 54 and ADC 56, and a calibration pulse. Of course, the cuff pressure involves an input from the subject shown in the box at the left of FIG. 10 The subject also inputs into the data acquisition and processing unit biographical data such as the subject's age and sex. The subject also inputs various operational commands or interactive steps such as commanding the volume plethysmograph to start or restart and stop.

As for the outputs, the data acquisition and processing unit produces three general outputs that are visible to the subject and shown diagrammatically as the subject in the dashed box on the righthand side of FIG. 10. These outputs include a normal operation indicator which is a green light or light emitting diode (herein LED) and a single beep as an audio signal, an abnormal operation indicator which indicates a motion artifact or a loose cuff. The motion artifact generates a red light indicator and a multiple beep. The loose cuff signal illuminates a red indicator light labeled "LOOSE CUFF" and the unit further provides a different multiple audible beep. The data acquisition and processing unit further outputs evaluated data that corresponds to a bar display that will be discussed hereinafter.

FIG. 11 diagrammatically illustrates the pneumatic/electronic interface of the volume plethysmograph. Deflate signals and step deflate signals from the electronic controller (including microprocessor 58) are sent to pressure transducer 52 which interacts with pump 36 and needle valve 38 and electronic deflation valve 34 to regulate pressure in cuff 30. A high pass filter 60 and a low pass filter 62 receive signals from pressure transducer 52. The high pass filter passes pressure differential signals $\Delta P$, whereas the low pass filter passes blood pressure signals P to the electronic circuitry. A calibrate signal is sent to the 1 ml chamber 42 to enable calibration of the entire system. Safety valve 32 insures that the pressure in cuff 30 does not exceed 250 mm Hg. Since cuff 30 is wrapped around the subject's leg, the subject is part of this structured pneumatic system diagram.

FIG. 12 is an electronic structured diagram for the volume plethysmograph. The operator or patient starts the volume plethysmograph and it activates self-test routine 70. The main control unit 72 monitors the pressure differential $\Delta P$ and the normal blood pressure P through the analog to digital process unit 74. The average pressure and the pressure pulse are sent to main control 72. Main control 72 interacts with A to D process 74 via an electrical bus. Main control 72 also controls cuff control 76. Cuff control 76 generates inflate signals, deflate signals, step deflate signals and a calibrate signal to pump 36, chamber 42, needle valve 38, electronic deflation valve 34, and electronic valve 40 (associated with chamber 42)

Main control 72 also includes a save data process 78. Biographical data (age, sex, lifestyle, e.g., smoker or non-smoker) for the patient is input into the save data process 78. The save data process stores a representative electronic signal for blood pressure differential $\Delta P$, average blood pressure P, and calibration data electronic file (CALIB-file). The patient's specific pressure differential signal $\Delta P$, average pressure signal P, is stored in a separate data file for (DATA-file). Save data processing unit 78 also compiles a biographical data file for the patient. The three electronic files are sent to a signal process 80. Main control 72 instructs signal processing unit 80 to begin processing the information upon confirmation of the appropriate pressure levels and time lapse, as will be discussed hereinafter. Signal processing unit 80 generates an evaluation error file which is available to main control 72. Signal processing 80 utilizes statistical tables to correlate the relative degree of atherosclerosis of the patient under study based upon, for example, look up tables for target values representing normal levels of arterial compliance. Main control process 72 further cooperates with display control 82. Display control 82 generates an indicator signal such as a green indicator light representative of the absence of a very low probability of atherosclerosis in he patient under study, single and multiple audible beeps indicating various system conditions, a normal operation indicator light, an evaluate data indicator, a red indicator light indicating loose cuff, and a second red indicator light indicating a motion artifact. Display control 82 operates with a "check for artifacts" process 84.

FIG. 13 is a structured diagram showing the principal processes for the volume plethysmograph. The process begins at the step 90, obtain volume plethysmograph data (VPG) Various data are input into the obtain VPG process 90. For example, the pressure differential signal from the cuff, indicating that pulsatile blood flow, the blood pressure of the patient, and calibration data from the appropriate file. The real time pressure differential signal, average pressure is obtained from a data file. Step 92 removes trends (drift) in the signals.

The general operation of the volume plethysmograph is as follows. The patient wraps pressure cuff 30 around the calf of his/her leg. The patient then presses the start/restart button and the unit undergoes a self-test. The self-test checks microprocessing unit 58, memory units 60 and 62, display 64, ADC 56, the LEDs (light indicators), bar displays and audio generators (beepers) and ultimately displays a "system OK" indicator on the display. This indicates that the self-test is complete and the unit is ready for use. The unit then inflates pressure cuff 30 by starting pump 32. If the cuff pressure does not reach 70 mm Hg after a predetermined number of seconds of pumping, as determined by pressure transducer 52, differential amplifier 54, ADC 56, microprocessor 58, and the various memory devices, a red indicator light indicating "a loose cuff" will start blinking and multiple audio beeps will be emitted by the unit. The unit then deflates the cuff. The patient will then rewrap the cuff to a snug fit and press the start/restart button or otherwise stop the test.

If the cuff pressure reaches 70 mm Hg after a predetermined number of seconds (timed ultimately by microprocessor 58), the unit initiates a calibration routine. One (1) ml of air is suddenly introduced into the cuff via chamber 42 as controlled by electronic valve 40. The unit then measures the drop in pressure $\Delta P$ and calculates a calibration factor. The unit then starts recording the volume pressure signal from under the cuff and obtains a maximum volume signal, discussed later. Cuff inflation will stop when the volume pulse signal decreases to 20% of this maximum value or a cuff pressure of 225 mm Hg, whichever is lower. If the pressure reaches 250 mm Hg, due to an electronic or a mechanical failure, safety relief valve 32 is automatically opened relieving the pressure in the cuff.

As an example of this cuff inflation, reference is made to FIG. 7A. In that figure, it is noted that blood volume change increases as cuff pressure increases from 40 mm Hg to 50 mm Hg and to 60 mm Hg. At 60 mm Hg, volume change is at a maximum. When the cuff pressure is further increased to 70 mm Hg, the blood volume change decreases relative to all of the foregoing $P_c$ pressures (40, 50 and 60). The volume change further decreases at a cuff pressure of 90 mm Hg. The maximum volume signal in FIG. 7A occurs somewhere at or near 60 mm Hg. Cuff pressure in the volume plethysmograph system would continue to increase beyond 60 mm Hg level and stops when the blood volume change signal decreases to 20% of the maximum value or when $P_c$ reaches 225 mm Hg, whatever comes first. This $P_c$ level corresponds to a supra systolic pressure. In relation to FIG. 7A, this may be a cuff pressure somewhat less than 70 mm Hg.

The volume plethysmograph system then deflates the cuff stepwise in increments of 10 mm Hg with the aid of electronic deflation solenoid valve 34. The rate of pressure drop is preset to 2-3 mm Hg per second. The unit continuously monitors the cuff pressure and estimates the instant the solenoid valve should be closed to achieve approximately a 10 mm Hg drop. The volume pulse signal is recorded for 3-5 seconds after a 2-3 second stabilizing period at each cuff pressure level. The exact average pressure will be obtained at each such cuff pressure level. The pressure reading will be rounded off to the nearest integer value to determine average pressure P. The process is continued until the cuff pressure is reduced to about 50 mm Hg. During normal deflation procedures, a green LED indicator light will blink. Completion of the recording sequence is indicated by a single audible beep and the green LED indicator light will be turned off.

A sampling rate of two samples per second is utilized. A pressure change of a predetermined amount mm Hg per sample (a threshold) will signify a large motion artifact. Motion artifacts occur when the patient has moved thereby changing the limb about which is wrapped the pressure cuff and hence introducing a pressure change in the cuff. A smaller pressure change detected by a smaller motion artifact will be compensated for in the electronic signal processing. If a large artifact is detected, that is, a pressure change exceeding the large motion artifact threshold, the "motion artifact" red indicator light will blink and the unit will produce multiple audible sounds or beeps. The unit then inflates the cuff by 10 mm Hg so the missed recording or discarded recording subjected to the large motion artifact can be re-recorded at that discrete pressure level without the motion artifact affecting the input signal. The patient can be expected to refrain from introducing such motion artifacts during the length of the test. If more than five motion artifacts occur during the measurement, the cuff will be completely deflated.

To restart the procedure, the patient will have to press the start/restart button when or he or she is ready to take the test again. The automatic inflation and deflation, step deflation, and calibration are performed by a peristaltic pump and a digital servo loop controlled by microprocessor 58. The patient can terminate the procedure at any time by pressing the stop button. At the time the cuff will be deflated. The volume pulse and cuff pressure signals at each 10 mm Hg cuff pressure levels and the calibrate signal are stored in the memory.

As shown in FIG. 13, remove trend step 92 de-trends these signals. In step 94, the signal is differentiated, and a maximum slope is found with respect to time. Step 96 defines the volume pressure pulse or cycle. This could be a window about the critical portion of each cycle. Referring again to FIG. 7A, in order to average the signal, it is necessary to detect the steep upward leading edge slope of each pulsatile flow signal to enable multiple signals per $P_c$ to be averaged. A time based differentiation of the input signals identifies the steep leading edge slope of the volume pressure signal and, accordingly, cycles beginning at that steep leading edge slope identify the critical portion of the pulsatile flow curve. When the differentiated signal exceeds a threshold, the resulting cycle time point can be used to overlay or average multiple cycles.

Step 98 overlaps and averages multiple signals at each discrete pressure level. Step 110 determines the volume change.

Equation 3 below is one way to determine the volume change.

$$\Delta V = \Delta P(V_b/1.4\, P) \qquad \text{Eq. 3}$$

where $\Delta V$ is in ml. Equation 3 assumes an adiabatic expansion. $V_b$ is the cuff bladder volume in ml, P is the absolute cuff pressure in mm Hg, and $\Delta P$ is the height of the cuff pressure oscillations due to limb volume change in mm Hg. Of course, since there is a pulsatile blood flow through the arteries of the limb, the cuff pressure oscillation is directly related to the blood volume differential.

A more appropriate expression for the present volume plethysmograph system is found in equation 4.

$$\Delta V = (\Delta P V)/(nP) \qquad \text{Eq. 4}$$

In equation 4, n may vary between 1 and 1.5 since for continuous/step wise pressure drop utilized in the present method, the expansion may be a combination of isothermal and adiabatic expansion. See J. G. Webster, Ed. *Medical Instrumentation, Applications and Design,* Houghton Mifflin Co., Boston, 1978. The automatic calibration procedure is utilized to account for the uncertainty of n under all circumstances including the specific protocol set forth herein. The 1 ml injection of air pressure by chamber 42 and electronic valve 40 into the cuff at any particular time can be utilized to further calibrate the signals. The drop in sensed pressure $\Delta P$ (that is, the drop as noted in FIG. 7a) will be measured. For typical values of cuff bladder volume $V_b = 500$ to 1000 ml, pressure P is approximately 860 mm Hg, and $\Delta V = 1$ ml, $\Delta P_{cal}$ will be between 1 to 2 mm Hg. There is a need for a calibration constant to convert $\Delta P$ recordings to $\Delta V$. The calibration constant K can be obtained by determining the proportional relationship between $\Delta V_1 = \Delta P_1 K$ as compared with $\Delta V_2 = \Delta P_2 K$, particularly when $\Delta V_1$ is known due to injection of the ml of air into the cuff.

Practically, a 1 ml chamber can not be precisely tooled and the electro-mechanical coupling may cause a change from the 1 ml chamber standard. This tooling error and system error is accounted for by an initial calibration with a precise 1 ml reference. This initial calibration will lead to a multiplicative constant A that will change K to $A \Delta P_c$.

Automatic calibration leads to quantification of limb volume change $\Delta V$ at different cuff pressures or induced pressure levels. Referring to FIG. 4 the arterial volume/cuff pressure or transmural pressure curve, as cuff pressure $P_c$ increases, the transmural pressure of the artery decreases and the pulse pressure $\Delta P$ (that is, the systolic pressure minus the diastolic pressure) traces different parts of the V-P (volume-pressure) curve. If N is the number of cuff pressures used, a curve similar to that shown in FIG. 4 can be obtained using the N data points for arterial volume and cuff pressure. These N data points are shown in FIG. 4 as $S_1, S_2, \ldots$. It can be assumed that the V-P curve has a piece wise-linear fit where the slope $S_k$ is constant for the k pressure increment of 10 mm Hg, where $k = 1, \ldots, N, N-1$. There are N simultaneous linear equations:

$$\Delta V_l = \sum_{K=1}^{N-1} A_{l,k} S_k \qquad \text{Eq. 5}$$

where $l = 1, \ldots, N-1$. Coefficient $A_{l,k}$ equals the number of mm Hg of $\Delta P$ that traces the V-P curve with slope $S_k$, for obtaining $\Delta V_l$. Thus, for the 35 mm Hg pulse shown in FIG. 4, $\Delta V_8 = 10\ S_8 + 10\ S_7 + 10\ S_6 + 5\ S_5$.

For transmural pressures higher than those tested, that is beyond $S_{14}$, the dashed line in FIG. 4, it can be assumed that the slope is constant and equal to $S_{n-1}$. This is a reasonable assumption because at those physiological transmural pressures, those corresponding to cuff pressures between zero to 40 mm Hg, the curve is reasonably linear. Cuff pressure signals less than 40 mm Hg are difficult to obtain because the cuff does not contact the limb sufficiently tight to adequately detect the pulsatile flow of the blood through the artery.

The set of simultaneous linear equations is expressed as $[\Delta V] = [A] \times [S]$, where $\Delta V$ is an $(N-1) \times 1$ matrix, with the A and S matrices being respectively $(N-1) \times (N-1)$ and $(N-1) \times 1$. Matrix inversion of A followed by multiplication times $\Delta V$ yields the unknown slopes for $S_k$, from which it can be computed that the lth volume $V_l$ at the lth transmural pressure $P_l$ is equal to $P_s - P_o + (1-1)\ 10$, where $P_s$ is equal to systolic pressure and $P_o$ is equal to the occlusion pressure at which there is no discernible volume impedance pulse detected. For the example in FIG. 4, the respective values are 110 and 160 mm Hg. The V-P curve can be obtained by plotting the internal arterial volume $V_l$ at discrete transmural pressure increments of 10 mm Hg.

There is a signal variability due to smooth muscle tone and short term fluctuations in the patient's blood pressure Accordingly, resulting V-P curve is smoothed with a cubic polynomial spline and a smoothing parameter of 15 and an error specification of 10% for the data on volume change. See "Routines for smoothing empirical data with splines, supplemental program series: SMOSP1, SMOSP2, and SMOSP3," Madison Academic Computing Center, University of Wisconsin, Madison, 1973.

In order to check the method of analysis, a known volume-pressure curve was utilized. A hypothetical pulse of 40 mm Hg was input as an assumption, and volume change at cuff pressure increments of 10 mm Hg was obtained. These results were fed into the aforementioned analysis as raw data for matrix inversion. The output was then fed into the smoothing program. The peak compliance after matrix inversion was the same as that of the original curve. The peak compliance after smoothing increased by 9.5%.

Some problems were detected in the analysis. For example, the cuff does not provide adequate contact with the limb at lower cuff pressures such as those below 50 mm Hg. During step wise inflation and step wise deflation, $\Delta P$ recordings are made at different cuff pressures. If $\Delta P$, at cuff pressures $P_c$ of 30, 40 or 50 mm Hg, is less than half the amplitude at cuff pressure 60 mm Hg, the recordings at those cuff pressures and lower cuff pressures are discarded. The volume-pressure plot was obtained with the remaining data.

Utilizing the volume plethysmograph, arterial volume change versus cuff pressure waveforms can be plotted and then classified according to the waveforms identified in FIGS. 8a, b, c and d. Otherwise, peak compliance of the artery can be ascertained. Referring again to FIG. 4, compliance at different pressures are obtained as the slope of the volume-pressure curve. The compliance is also obtained as a ratio of the limb volume change at the cuff pressure to the pressure pulse (systolic minus diastolic) causing the limb volume change. The peak compliance is determined as the maximum slope of the volume-pressure curve or the value determined as the ratio of the maximum limb (mainly arterial under these conditions) volume change to the pulse pressure causing it. To validate the volume-pressure curve, peak values obtained from the volume plethysmograph and the electrical impedance plethysmograph must agree within plus or minus 10% of each other. The volume-pressure curve is also used in additional computations and in conjunction with additional parameters. These additional parameters and computations were obtained based upon the human and monkey studies discussed hereinabove. In order to determine the mathematical relationship between peak compliance, age, blood pressure and an ascertained degree of atherosclerosis for a particular patient, data from the human subject study previously discussed herein and the monkey study data also previously discussed herein was pooled together.

Returning to FIG. 13, interpolate and generate ΔV and cuff pressure curve step 112 . is discussed hereinabove. Calculate parameter step 114 utilizes statistical tables and interpretation step 116 uses biographical data obtained from the patient. The interpret step also places the data in an evaluation/error file.

In order to ascertain whether the patient under study has an unacceptable amount or degree of atherosclerosis, a comparison must be made between a target value and a computed patient value. This method is different than the waveform classification discussed earlier. The method discussed immediately herein involves utilizing the obtained peak compliance of the artery and other biological data collected from the patient.

In a preferred embodiment, the target compliance $C_T$ is based upon the patient's age A in years, limb circumference in cm and the detected systolic pressure or established systolic pressure of 120 mm Hg (considered normal for a human) as shown in equation 6 which follows.

$$C_T = K - 0.0331(SYST - BP) - 0.0143(A) - 0.726\left(\frac{12.56(240)}{L^2}\right) \quad \text{Eq. 6}$$

where SYST-BP=systolic blood pressure (normally 120 mm Hg), A=age of patient, L=limb cm circumference under cuff, and K=a constant.

The regression coefficients 0.0331, 0.0143, and 0.121 [associated with Z] were obtained from the human study. The peak compliance and the systolic pressure, age, and limb circumference yielded the highest correlation coefficients.

Since it is convenient to also discuss the target compliance in conjunction with electrical impedance plethysmograph at this time, equation 7 below provides the mathematical correlation between peak compliance and these factors.

$$C_T = K - 0.0331\ (SYST\text{-}BP) - 0.0143(A) - 0.726(Z) \quad \text{Eq. 7}$$

where Z=tissue impedance in ohms per unit length, cm.

The relationship between equations 6 and 7 is found in the following equation 8. Essentially, equation 8 converts limb circumference, which is a physical factor affecting the pressure signal detected by the volume plethysmograph, into a tissue impedance factor which is a physical factor affecting the signal obtained by the electrical impedance plethysmograph.

$$Z = 240/\pi(L/2\pi)^2 \quad \text{Eq. 8}$$

The range for asymptomatic subjects will be considered to be target compliance $C_T$ plus or minus 10%. The intra-subject variability is 10%. Thus, if peak compliance $C_P$ is greater than 1.2 $C_T$, the subject has significantly less atherosclerosis than an average subject.

The blood pressure increases as an asymptomatic person ages. The fixed value of 120 mm Hg for systolic pressure (SYST-BP) used in the foregoing equations is preferably replaced with an appropriate value for a particular patient age group. There are conversion tables available to obtain these age group values.

To further quantify the degree of atherosclerosis, monkey study data is extrapolated to human subjects. An estimate of the extent of iliac disease and the disease in all major arteries including iliac arteries is determined. For iliatic arteries, equation 9 is utilized.

$$ILIAC\text{-}DISEASE\text{-}EXTENT = (94.5 - 6.6\ C_p - 1.25\ HDL)1.5 \quad \text{Eq. 9}$$

where $C_p$=peak compliance and HDL=high density lipoprotein cholesterol level.

If the patient's HDL or cholesterol level is not know, an appropriate average for the patient's age group will be utilized. These values can be found in currently available tables. The foregoing mathematical equation was obtained from the multiple linear regression of the monkey study data and represents the constants and the regression coefficients for PK-CMPL, and α-cholesterol.

Equation 10 below correlates the major disease extent to peak compliance and cholesterol level. Again, the constant in equation 10 and the regression coefficients were obtained from the multiple linear regression data obtained from the monkey study data.

$$Major\text{-}Disease\text{-}Extent = (84.4 - 6.2\ C_p - 0.73\ HDL)1.5 \quad \text{Eq. 10}$$

Values lower than 0% will be designated as 0%. Values higher than 100% will be designated as 100%. The average of these two computations for iliac disease extent and major disease extent are used to represent the total disease extent or average disease extent. This is found in equation 11 which follows.

$$ADE = AVE\text{-}Disease\text{-}Extent = (89.45 - 6.4\ C_p - 0.99\ HDL)1.5 \quad \text{Eq. 11}$$

The constants in equation 11 are simply the average of the constants in equations 9 and 10.

Equation 12 below is the ideal disease extent (IDE) which correlates the target compliance, asymptomatic or "ideal condition" for the patient.

$$IDE = (89.45 - 6.4\ C_T - 0.99\ HDL)1.5 \quad \text{Eq. 12}$$

For the ideal disease extent, an average cholesterol level HDL should be utilized for the patient's age group. Both ADE and IDE will have 0% and 100% as lower and upper limits, respectively. The values beyond the limit levels will be designated as limit values.

The evaluation of the patient under study is given as a range and, therefore, must be normalized. Equation 13 that follows is a standard normalization equation.

$$Display\ Value = 100 - (ADE/IDE)50 \quad \text{Eq. 13}$$

Table 6 below shows ADE/IDE levels ranging from 2.0 to 0.0 and display levels in increments of 10%. In the right-hand column, there are green, yellow and red light indicators that visibly show the patient the quantitative extent of atherosclerosis.

TABLE 6

| ADE/IDE | DISPLAY | COLOR |
|---------|---------|-------|
| 0.0 | 100% | Green |
| 0.2 | 90% | Green |
| 0.4 | 80% | Green |

TABLE 6-continued

| ADE/IDE | DISPLAY | COLOR |
|---------|---------|-------|
| 0.6 | 70% | Yellow |
| 0.8 | 60% | Yellow |
| 1.0 | 50% | Yellow |
| 1.2 | 40% | Yellow |
| 1.4 | 30% | Yellow |
| 1.6 | 20% | Red |
| 1.8 | 10% | Red |
| 2.0 | 0% | Red |

Since the target compliance value can be related to a chronological age or age group and/or a systolic blood pressure group for an age group which includes the age of the patient, the target compliance value can be located in a look-up table rather than calculated. The target value for the patient is based on a quantitative analysis of arteries possessing different degrees of atherosclerosis. This target value is a combination of the IDE equation and the target compliance $C_T$ equations, that is, equations 6 (or 7) and 12. The target value preferably includes at least the patient's age or age factor, a blood pressure value either systolic or diastolic, or a cholesterol factor based on a normal value for HDL within the patient's age bracket or a normal value for LDL within that bracket. The tissue volume factor Z or limb circumference L is preferably included in order to normalize the signal from patient to patient. The relative degree of atherosclerosis compares the target value with a patient's specific value. This patient specific value . is essentially the ADE or average disease extent that is related to the peak compliance measured from the arterial blood flow and the pressure differential. Since peak compliance varies with at least age and may vary based upon the systolic or diastolic pressure of the patient and the patient's cholesterol level, the relationship between the peak compliance of the patient and one of these other factors is preferably used to determine the relative degree of atherosclerosis in combination with the ascertained target value.

Enhanced ZPG System

FIG. 14 is a block diagram of an enhanced system utilizing an electrical impedance plethysmograph. FIG. 14 shows pressure cuff 210 wrapped around the leg of a patient. A 3-channel impedance plethysmograph 212 (ZPG) is used to record signals from the patient. Essentially, an oscillatory current is sent via ZPG port I1 to electrode 212 on the patient's limb. The current passes through both of the patient's legs and returns to ZPG 212 via electrode 214 and port I2. Ports V21 and V22 sense voltage changes due to the high frequency oscillatory currents sent between I1-I2. Impedance pulses are also obtained via ports V12 and V11 (electrodes 216, 212) and via ports V31 and V32 (electrodes 220, 221). The signals output from the machine have an amplitude range of plus or minus 10 volts and a frequency range of 0.1 to 30 Hz for humans. In monkeys, a range of 0.1 to 100 Hz is noted. The impedance pulses are acquired at a sampling rate of 1 kHz to extract timing relationships amongst the simultaneously recorded signals.

To calculate limb volume change from the impedance plethysmograph recording, data and signals are obtained on the tissue impedance of a limb segment. This tissue impedance is obtained from electrodes 216 and 218 coupled to ports V12 and V11 or electrodes 220 and 221 coupled to ports V31 and V32. Accordingly, three 10 bit digital inputs must be applied to data acquisition and storage unit (DAS) 230. The sampling rate required is much lower, that is, once for each discrete cuff pressure level, since the tissue impedance does not change much from one signal acquisition period to the next on the same subject.

An operator pumps up pressure cuff 210 on the leg to different discrete cuff pressure levels under the guidance of the electronic system. This requires an additional analog channel to monitor the pressure transducer output during set-up for each cuff pressure. This analog channel is noted by line 232. The impedance pulse recording is made within five seconds with the patient holding his or her breath at the end of normal expiration. The holding of the patient's breath reduces variability in the recorded signal. The operator initiates the data collection only after an indication from the subject. The cuff is then deflated and the recording is repeated at the next higher cuff pressure in 10 mm Hg increments. The process terminates when no discernible recording is made for the limb segment under the cuff. A particular recording is repeated if there are motion artifacts identified by the system from the resulting fast changes in the impedance signal or if the data collected is deemed unsatisfactory from a visual inspection of the graphic display of the collected data. The graphic display is provided on a Hewlett-Packard 7470 plotter 234. Printer 235 is capable of producing a printed record. Data is also recorded on a floppy magnetic disc between recordings and later processed off-line.

In the off-line processing, first the drift in the recordings is removed (de-trending the signal) followed by signal averaging to reduce the effect of other physiological parameters. The averaged signals are used to determine the arterial volume change, propagation delay, blood pressure, arterial volume-pressure curve, etc. The system is a menu driven system The system further provides timely reminders to the operator about other measurements, such as blood pressure measurement using the Korotkoff method, feedback on motion artifacts so the operator can repeat the experiment, the next step in the data collection, etc. The microprocessor or computer used in the present system is a MACSYM 150 system which is identified as processor 236 in FIG. 14. Computer 236 is an 8086/8087-base system. It is a measurement and control system from Analog Devices, Inc. It is based on a MP/M-86, a multitasking, single user (for MACSYM) operating system that is a superset of CP/M-86. MACBASIC (measurement and control BASIC) is an enhanced version of BASIC that approaches the speed of compiled languages and has extensions for assessing analog and digital I/O (input/output) ports. It also provides special commands to support graphics. The analog input and output cards have a 12 bit resolution and provide an adequate number of channels. The digital I/O board provides 16 digital I/O ports. In addition, the system has 256 kbytes of RAM, a dual floppy drive, a CRT monitor, and supports RS-232 and IEEE-488 interfaces for communication purposes.

Data acquisition and storage unit (DAS) 230 is utilized in conjunction with computer 236 because the computer cannot support a programmed data transfer rate of 1 kHz for three channels.

The diagrams and flow charts/pseudo-code disclosed herein permits a hierarchical top down approach of defining lower levels of interfaces. At these lower levels of interfaces, especially for PC computer 236 and DAS 230, hardware and/or software systems can be implemented. Structured analysis permits building such structured specifications. See T. Demarco, *Structured Analysis and System Specification*, Yourdon, Inc., New York, N.Y. (1978) and C. McClure, *Case in Software Automation*, Prentice Hall, Englewood Cliffs, N.J. (1989). Structured analysis uses data flow diagrams (DFD) data dictionaries and high level process documentation. A data flow diagram shows flows of data, not control. It shows only the set of possible paths, and does not provide information on which path will be followed or what initiates a given process. A data dictionary documents each of the interface flows and data stores on any of the data flow diagrams.

A DFD is comprised of the following four elements: Data flows, represented by named vectors; Processes represented by circles; Files represented by straight lines; and Data sources and sinks, represented by boxes. A source or a sink lies outside the context of a system and is a net originator or a receiver of system data. FIG. 15 is a top-level DFD of the system. As implied, the DFDs have hierarchical levels. FIG. 16 shows the intermediate level DFD, while FIGS. 17, 18 and 19 represent the lowest level DFDs with the most detail. A program called "Software through Pictures" developed by Interactive Development Environments, San Francisco, Calif., was used on an HP), is used to develop the DFDs. Data flows into and out of a bubble (process) on a parent diagram are equivalent to net inputs and outputs to and from a child diagram. Thus, OPERATOR INTERACTION in FIG. 15 is equivalent to (PATIENT INFO (410)+GEN-V-P (412)+COMP-V-P (414)+COLLECTION & STORE (416)) in FIG. 16. See the following entries in the Data Dictionary presented in Table 7 which follows:

menu, the acquired waveform, and run time information. See Table 8 which follows.

TABLE 8

Functional Subdivision (Quadrants) of the Monitor Screen during Data Acquisition 1. Menu (upper left quadrant - ULQ)
2. Waveform (URQ)
3. Run Time Information (LLQ)
4. Open (LRQ)

Table 9 shows the details of the menu quadrant for the data acquisition process. Soft keys or function keys F1–F8 are used for making selections.

TABLE 9

Detail of Menu-Quadrant Screen Sector during Data Acquisition

| Key | Function |
|---|---|
| F1 | READ Ch1 |
| F2 | READ Ch2 |
| F3 | STORE |
| F4 | NEXT |
| F5 | DONE |
| F6 | CALIBRATE |
| F7 | GO BACK |
| F8 | CHECK |

Prompt: SELECT
Prompt: Pump Cuff Pressure to 20 and Return

A typical sequence is as follows. The operator pumps up the cuff to 20 mm Hg and presses RETURN. The MACSYM reads the pressure (CUFF-PR-SIG (FIG. 15), CUFF-PRESS (FIG. 16), CUFF PRESS (FIG. 17)) from the corresponding pressure transducer (trans-

TABLE 7

```
OPERATOR_INTERACTION::=PATIENT_INFO+COLLECT&STORE+GEN_V_P+COMP_V_P
DISPLAY_DATA::=DISPLAY_DATA1+DISPLAY_DATA2+DISPLAY_DATA3
PRINT_DATA::=PRINT_DATA1+PRINT_DATA2
PULSE::=IMPED_PULSE+TISS_IMP
DISPLAY_DATA1::=MENU1+D_IMPED_PULSE
DISPLAY_DATA2::=MENU2+D_IMP_DATA+DETRENDED_DATA+DIFFERENTIATED_DATA
    +VOL_CHANGE+D_DV_CP_DATA
DISPLAY_DATA3::=MENU3+D_V_P_DATA+D_COMP_DATA
PRINT_DATA1::=PR_DV_CP_DATA+RAW_DV_CP_DATA
PRINT_DATA2::=PR_V_P_DATA+PR_COMP_DATA
PLOT_DATA::=PL_V_P_DATA+PL_COMP_DATA
```

In FIG. 17, low level DFD for data acquisition and storage is illustrated. These operations are menu-driven. The collected data are checked for motion artifacts (1.1.4) and automatic resets by slope determination and thresholding (See T. M. R Shankar and J. G. Webster (1984b), "Design of an automatically balancing electrical impedance plethysmograph," J. Clin. Eng., 9:129-134). The data is accepted if the slope is less than 50 V/s. These details, not show here, are included in the 'Process Description' for the CHECK FOR ARTIFACTS (1.1.4) process. The operator may change the threshold by an appropriate control.

Interactive Menu Driven System

The system is designed to be completely menu driven and implements a hierarchical system where function (soft) keys are used to invoke different options at different levels. As seen in FIGS. 17, 18 and 19, operator interaction with the MACSYM PC 236 is implicit in most of the steps.

The screen of the CRT monitor was divided into four quadrants, with three quadrants used to display the ducer 3, FIG. 15) and informs the operator to inflate/deflate the cuff so the pressure is within 1 mm Hg of the desired pressure. This information will appear in the lower left quadrant of menu Table 8. The operator chooses READ CH1, READ CH2 by pressing key F1/F2 (Table 9) only after appropriate completion of this step. Then the operator invokes F1/F2 to acquire data from a channel. The data collection is initiated only after the subject and operator indicate that data collection may start. The acquired waveform (at maximum programmed data transfer rate of 706 Hz for single channel) will appear in the right top quadrant of menu Table 8. If there are strong or large motion artifacts, the system beeps and displays a message in the lower left quadrant (herein LLQ) of menu Table 8. If not, the operator visually ascertains the quality of the acquired waveform. If acceptable, the operator invokes STORE key F3 (Table 9) to store it on a floppy disc. If not, key F7 GO BACK is invoked. After successful completion of the step, key F4 NEXT is invoked to record at the next higher cuff pressure. Key F6 CALIBRATE provides an on-line calibration of the system and particularly the instrument, while invocation of key F8

CHECK lists the subset of experiments completed up to that point. The list is displayed in LLQ of menu Table 8. At the end of the whole set of experiments, key F5 DONE is invoked. The system updates the patient (subject) file on the floppy disc and the test is terminated. Control returns to a higher level menu where other types of tests may be chosen or the session terminated.

Algorithms Used

Data so acquired is processed off-line with subroutines for trend removal (REMOVE TREND (1.2.4) FIG. 18), signal differentiation (DIFF. & FIND MAX SLOPES (1.2.5)), and signal averaging (COMPUTE AVERAGE SIGNAL (1.2.6)), all illustrated in FIG. 18.

The output from ZPG 212 has a tendency to drift, as shown graphically by the base line drift in FIG. 20a.

Figure 20B:
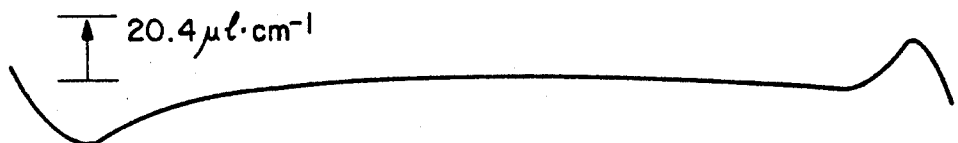
Figure 20C:
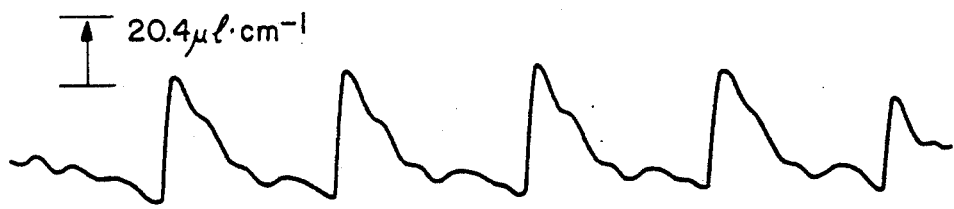

To remove drift in the acquired signal, a triangular window is used first to obtain a moving average (i.e., low pass filtered signal). See FIG. 20b and REMOVE TREND (1.2.4) in FIG. 18. This base value (moving average) is then subtracted from the original signal to determine the de-trended (or high pass filtered) signal (See D. G. Childers and A. Durling (1975), *Digital Filtering and Signal Processing*, West Publ. Co., St. Paul, Minn., 315-318. See FIG. 20c and DETREND-DATA output from process 1.2.4 in FIG. 18. To obtain a larger bandwidth for the de-trended signals, a lower cut-off frequency and hence larger time-window is needed. This, however, results in more computation time. A cut-off frequency was selected to be as large as allowable (0.45 Hz). A direct implementation of the algorithm required 46 minutes to complete the calculations of 4 k of data. In order to reduce the computation time, every eighth sample of the data was used. This reduced the number of data points from 4 k to 512. This in turn bandlimited the low-pass filtered (with moving average) signal to 44.12 Hz (maximum programmed data transfer rate for MACSYM 150 is 706 Hz). Interpolation was used to find intermediate points, assuming that the moving average (trend) slope was constant for the intermediate points. This effectively restores, at least sufficiently for the present equipment and test, the bandwidth to 353 Hz. Computation with this modified algorithm takes less than three minutes. Note that the de-trended signal is distorted at the boundaries. See FIG. 20c. The computation period could be further reduced to 0.5 min by using a second analog channel with input from the low-pass filtered (analog filter, cut-off frequency of 0.45 Hz) signal.

Figure 20D:
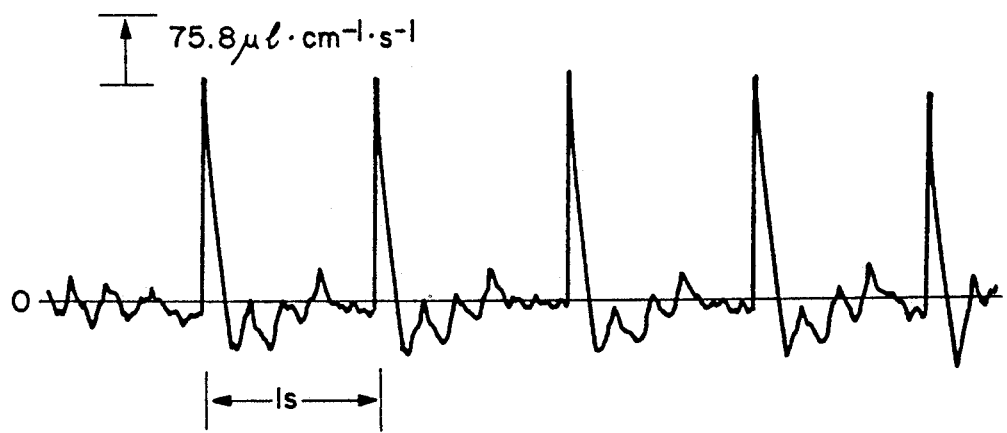

The signal is then differentiated (3-point difference) (See Diff. (1.2.5), FIG. 18) and zero crossings are detected, to determine the foots of the systolic upswings and accordingly, the individual cycles. See Define cycles (1.2.6), FIG. 18. FIG. 20d shows the differentiated signal. The cycles are then overlapped, taking the maximum slope points (during systolic upswings) as the reference points for overlapping, and averaged. See Compute Ave. Sig. (1.2.7), FIG. 18. The first and last cycles were discarded because of de-trending distortion. Compare, for example, the first and last cycles of FIGS. 20(a) and FIG. 20c.

The foot-to-peak amplitude of the averaged or overlapped signal yields the impedance pulse height $\Delta Z$ (FIG. 14) which was then used to determine the arterial volume change $\Delta V$. The volume-pressure curve is then determined using matrix inversion, discussed earlier herein. The implementation was based on a BASIC program from T. E. Shoup (1983), *Numerical Methods for the Personal Computer*, Prentice-Hall, Englewood, N.J., 50-52.

FIG. 21 shows a set of arterial volume change signals, under pressure cuff 210 on the patient's limb (FIG. 14), at different cuff pressures. FIG. 22 shows recordings in a limb segment distal to the pressure cuff. These distal readings are obtained from electrode pair 216, 218 at ZPG inputs V12 and V11. See I. O. Cikikci (1986), *A Data Acquisition and Processing System for the Study of Peripheral Vascular Dynamics*, MS thesis, Dept. of Electrical and Computer Engineering, Florida Atlantic University, Boca Raton, Fla. for more details.

Hardware Approaches

MACSYM 150 (PC Computer 236) cannot be used for simultaneous data acquisition at reasonably high rates (1 kHz or above) from several channels. For such experiments, a 3 channel simultaneous data acquisition system (DAS) 230 using a 8748 micro-controller 530 was developed. See FIG. 23. The DAS 230 services requests from and communicates with MACSYM 150 via digital I/O ports. The DAS 230 has four 8-bit A/D converters, three with dedicated memories (4 kbytes each) for simultaneous acquisition and storage of impedance pulses and one for obtaining the cuff pressure. DAS 230 has a sampling rate of 1 kHz and permits collection of 4-5 cycles of impedance pulses. The RAM was further increased to 8 kbytes to record 7-8 cycles. The sampling rate can be increased to 10 kHz.

MACSYM communicates with DAS through the following primitives:

---
OBTAIN AND SEND CUFF PRESSURE
OBTAIN AND STORE IMPEDANCE PULSES
SEND IMPEDANCE PULSES: CH1-CH3
SEND TISSUE IMPEDANCE: CH1-CH3
---

In the impedance plethysmograph, MACSYM communicates with the DAS through the primitives given above. The aim of the DAS is to bring in all the parameters to MACSYM where further analysis of the data can be made. The primitive OBTAIN AND SEND CUFF PRESSURE is involved to read the cuff pressure value.

The task of reading in impedance pulses ($\Delta Z$) is accomplished in two stages, one being to simultaneously acquire and store data into the 3 channels of DAS with the primitive OBTAIN AND STORE IMPEDANCE PULSES. The second stage is to transfer the stored data from DAS to MACSYM with the primitive SEND IMPEDANCE PULSES. The tissue impedance (Z) can be read by invoking the primitive SEND TISSUE IMPEDANCE.

The listing of the source code for the 8748 micro-controller 530 and the program listing for the MACSYM to control the DAS is complied using M. S. Kolluri, I. O. Cikikci and R. Shankar (1988), *Three-channel Simultaneous Data Acquisition System*, Technical report, Dept. of Electrical and Computer Engineering, Florida Atlantic University, Boca Raton, Fla.

Acquisition of the Cuff Pressure

When MACSYM requires the cuff pressure it sends a convert ($\overline{CONV}$) signal to the 8-bit A/D converter (ADC 510). See FIG. 24. The cuff pressure is converted to a voltage signal through the pressure transducer 512 (0-5 psi, gage, with a sensitivity of 10 mV/psi), which is then amplified with a differential amplifier (gain of 100), and input to the ADC. After the A/D conversion is over, the conversion completion is indicated by the ADC via the $\overline{\text{INT}}$ signal to the 8748 micro-controller 530 in FIG. 23. Controller 530 pulls the $\overline{\text{MWR}}$ signal low so the digital value will be available at the input to the tri-state buffer 532 in FIG. 24. Then 8748 controller 530 indicates the availability of the data to MACSYM. MACSYM then pulls the enable signal at EN port of the tri-state buffer 532 low, reads in the data through the digital I/O port (DIO bits 0-7). M. S. Kolluri, I. O. Cikikci and R. Shankar (1988), *Three-channel Simultaneous Data Acquisition System*, Technical report, Dept. of Electrical and Computer Engineering, Florida Atlantic University, Boca Raton, Fla. provides additional details for this process.

Acquisition of the Impedance Pulses

FIG. 25 shows the block diagram of the board for one data collection channel. There are three separate channels with the same configuration for acquiring the data into the three channels simultaneously and so all the A/D converted data is stored in RAM of that channel after every conversion. After the required amount of data is collected (here 8 kbytes) the DAS 230 responds to the command to read in the stored data into the MACSYM. This "reading in" process is done serially one channel at a time. The tissue impedance Z which is already a digital signal from the impedance plethysmograph can be read in by enabling the tri-state buffer.

The schematic of a data acquisition and storage channel of the DAS is given in FIG. 26. The analog input, AIN, originates from the impedance plethysmograph output ($\Delta Z$) of that channel. The schematic does not include the interface for reading the tissue impedance Z.

When the input signal is set up, $\overline{\text{CONV}}$ signal is pulled low by the micro-controller 530 and after the A/D conversion is completed the interrupt signal $\overline{\text{INT}}$ from ADC 510 goes low and the digital data is put out on its output lines. The 8748 Controller 530 senses this signal on controller port TO (see FIG. 27) and pulls $\overline{\text{MWR}}$ input to SRAM 550 (FIG. 26) low and simultaneously sets up the address. After a certain delay, $\overline{\text{MWR}}$ is pulled high. For reading out the data from the SRAM 550, the G ($\overline{\text{CHxR}}$) signal is pulled low by the 8748 controller 530 which enables the intermediate inverting buffer too, and data will be read into the digital I/O port (DIO bits 0-7) of the MACSYM.

The micro-controller (8748) circuit 530 controls the simultaneous data acquisition for 3 channels and establishes handshaking with MACSYM for communication to service requests and transfer of data.

The 8748 Micro-controller

The schematic of the controller circuit and the configuration of its two I/O ports (P1 and P2) and its BUS ports of the 8748 micro-controller 530 is shown in FIG. 27. The 8 lines of the BUS port on the controller and least significant 5 lines of port 2 of the controller are used to generate the address for the RAM 550 on each of the channels. Six lines of port P1 of the controller are used to establish handshake between the micro-controller and MACSYM. Lines 5 and 6 of port P2 are used for $\overline{\text{CONV}}$ and $\overline{\text{MWR}}$ to control the sampling rate and storing in of data in each of the channels respectively. The interrupt signal $\overline{\text{INTx}}$ from the A/D 510 (FIGS. 26 and 27) is used to set the flag signal port TO of 8748 controller 530 to indicate the completion of conversion of one sample of data.

The timing sequence to establish handshake with MACSYM and transfer of data is shown in timing diagram FIG. 28. The handshake is established by MACSYM initially pulling DIO (digital I/O) bit 10 (FIG. 28a) low. Controller 530 responds by pulling DIO (FIG. 28b) bit 9 low. This is read by MACSYM and it now sets up the task to be performed (one of the 8 primitives) on DIO bits 13-15 (FIG. 28c) and pulls DIO bit 10 (FIG. 28a) high Controller 530 reads the task information after sensing DIO bit 10 as high and goes to the corresponding routine (FIG. 28d).

Assume the task now is to store data samples in RAM after A/D conversion. This task is performed solely by the controller and does not involve MACSYM. The $\overline{\text{CONV}}$ signal of A/D is pulled low (FIG. 26). After data conversion is over, $\overline{\text{INT}}$ of A/D (FIG. 28e) goes low and is sensed by the controller on its TO line, then $\overline{\text{MWR}}$ line is pulled low to allow data to be stored in RAM. Data is stored in all 3 channels simultaneously.

The tissue impedance Z is already a digital signal coming from the impedance plethysmograph and can be transferred to the MACSYM by enabling the intermediate buffer. If the task is to read cuff pressure, the $\overline{\text{CONV}}$ signal of ADC on the pressure channel is pulled low (see FIG. 24). The ADC 510 sends a low signal on $\overline{\text{INT}}$ (TO) to indicate 8748 controller the end of conversion.

The next step is to send the digital signals from DAS to MACSYM and is common to all the primitives of data transfer. The controller sets DIO bit 8 (FIG. 28f) low, which is detected by MACSYM and it in turn pulls DIO bit 11 (FIG. 28g) low. Note that the MACSYM would have set up earlier the task information (ID). The task ID specifies the data to be read in, i.e., impedance pulses $\Delta Z$ from channel 1/2/3, or pressure P, or tissue impedance Z from channel 1/2/3. That is the $\overline{\text{CHxR}}$ information. The controller responds by pulling DIO bit high and simultaneously pulling EN (FIG. 28h) to the decoder (LS138) low. One of the $\overline{\text{CHxR}}$ lines will go low corresponding to the channel to be read from. Data is placed on DIO bits 0-7 (FIG. 28i) of MACSYM. MACSYM reads the information into its memory. DAS will now be ready for a new command from the MACSYM. This handshaking process is repeated for every single byte of data. The description detailed above is depicted in the form of a flow chart in FIGS. 29, 30 and 31.

FIGS. 32 and 33 show such simultaneously recorded data. In this test, a pressure cuff was used as a voltage plethysmograph on the lower limb. An impedance plethysmograph was used to record the impedance pulsations from the central one-third of the cuff. ECG was used as the time reference. Recordings were made at 10 mm Hg increments in the cuff pressure.

FIGS. 21 and 22 show simultaneously acquired data from two different limb segments. Signals at different proximal cuff pressures have been overlapped with the aid of simultaneously acquired ECG as time reference.

The claims appended hereto are meant to cover modifications and changes within the spirit and scope of the present invention.

What is claimed is:

1. A method of detecting the onset of atherosclerosis comprising the steps of:
    changing blood flow through an artery with the application of differing amounts of induced pressure thereat;

sensing an arterial blood volume differential while said artery is placed under said differing amounts of induced pressure;

repeating said sensing step when a signal parameter representative of said blood volume differential exceeds a predetermined level;

determining whether a function of said volume differential and said differing amounts of induced pressure defines a waveform peak; and, generating an atherosclerosis indicator signal in the absence of said waveform peak.

2. The method as claimed in claim 1 wherein the step of sensing arterial blood volume differential includes the step of sensing arterial blood volume non-invasively while said artery is placed under differing amounts of induced pressure at discrete levels of induced pressure.

3. The method as claimed in claim 2 including the steps of:

sensing multiple arterial blood volume differentials at each discrete level of induced pressure;

disregarding a signal representative of said blood volume differential which exceeds said predetermined level; and, subsequently averaging said multiple differentials prior to the step of determining the absence of said waveform peak.

4. The method as claimed in claim 3 including the step of sensing a blood pulse remote from said artery under pressure and using the same as a representative timing signal to enable the step of averaging said multiple volume differentials.

5. A method as claimed in claim 4 including the step of providing an operator alarm signal when said representative signal exceeds said predetermined level.

6. A method of detecting the degree of atherosclerosis in an artery comprising the steps of:

changing blood flow through an artery with the application of differing amounts of induced pressure thereat;

sensing an arterial blood volume differential while said artery is placed under said differing amounts of induced pressure;

repeating said sensing step when a signal parameter representative of said blood volume differential exceeds a predetermined level and disregarding the corresponding blood volume differential;

relating said volume differential to said differing amounts of induced pressure;

correlating the volume differential-induced pressure relationship with one of a plurality of predetermined waveform shapes; and, generating one of a plurality of atherosclerosis indicator signals based upon the waveform correlation wherein each indicator signal indicates a different degree of atherosclerosis.

7. A method as claimed in claim 6 wherein said step of sensing includes the step of sensing non-invasively sensing said arterial blood flow while said artery is placed under differing amounts of induced pressure at discrete levels of induced pressure.

8. A method as claimed in claim 7 wherein the step of correlating includes the step of correlating said volume differential-pressure relationship with a plurality of predetermined waveform shapes including a plurality of waveform peak shapes and at least one substantially peak-less waveform shape.

9. A method as claimed in claim 8 including the step of providing an operator alarm signal when said representative signal exceeds said predetermined level.

10. A non-invasive method of detecting the relative degree of atherosclerosis in a patient comprising the steps of:

changing blood flow through an artery by placing relatively discrete levels of pressure on a portion of said artery;

non-invasively sensing blood volume as an impedance pulse in said artery at various induced pressure levels and generating an impedance pulse signal representative thereof, and obtaining a representative signal of a tissue impedance near said artery;

calculating an arterial blood volume differential from said impedance pulse signal and the tissue impedance signal;

sensing and calculating a blood pressure differential of the patient;

repeating the steps of sensing blood pressure differential and blood volume when a signal parameter representative of said blood pressure differential exceeds a predetermined level;

obtaining a peak compliance value by determining a maximal ratio of the blood volume differential and blood pressure differential by repeatedly obtaining the arterial blood volume differential at different induced levels of arterial pressures;

providing a target value related to at least one of a chronological age and an average systolic blood pressure for an age group about the age of said patient, said target value being based upon a quantitative analysis of arteries possessing different degrees of atherosclerosis;

determining and indicating the relative degree of atherosclerosis by comparing said target value with a patient specific value that is computed using a predetermined correlation incorporating said peak compliance value and at least one characteristic value from the group consisting of a detected systolic pressure, a detected diastolic pressure, an ascertained cholesterol level and the patient's chronological age, all obtained from said patient.

11. A non-invasive method of detecting atherosclerosis of a patient comprising the steps of:

changing blood flow through an artery with the application of discrete levels of induced pressure thereat;

obtaining an arterial blood volume differential by non-invasively sensing pulsatile blood flow through said artery while said artery is placed under discrete levels of inducted pressure;

sensing and calculating a pressure differential of the pulsatile blood flow passing through an arterial system that includes said artery;

repeating the steps of obtaining blood volume differential and sensing pressure differential when a signal parameter representative of said pressure differential exceeds a predetermined level;

obtaining a peak compliance value by determining a maximal ratio of the blood volume differential and the pressure differential;

providing a target value of said patient, said target value calculated using a first predetermined correlation incorporating at least the patient's chronological age factor, said first predetermined correlation derived form a quantitative analysis of arteries possessing different degrees of atherosclerosis;

calculating and indicating the relative degree of atherosclerosis by comparing said target value with a patient specific value that is computed using a second predetermined correlation with said compliance value and at least on e characteristic value from the group consisting of a detected systolic pressure, a detected diastolic pressure, an ascertained cholesterol level and the patient's chronological age, all obtained from said patient.

12. A method of detecting the degree of atherosclerosis of a patient under study comprising the steps of:

changing blood flow through an artery with the application of discrete levels of induced pressure thereat;

obtaining an arterial blood volume differential from said artery while said artery is placed under said discrete levels of induced pressure;

obtaining the patient's blood pressure differential;

repeating the steps of obtaining blood volume differential and pressure differential when a signal parameter representative of said pressure differential exceeds a predetermined level;

calculating a peak arterial compliance value by selecting the maximal ratio of said volume differential and said pressure differential;

providing a target value for said patient using a first predetermined correlation incorporating the patient's chronological age factor, said first predetermined correlation derived from a quantitative analysis of arteries possessing different degrees of atherosclerosis;

determining and indicating the relative degree of atherosclerosis by comparing said target value with a patient specific value that is computed using a second predetermined correlation incorporating said peak compliance value and at least one characteristic value from the group consisting of a detected systolic pressure, a detected diastolic pressure, an ascertained cholesterol level and the patient's chronological age, all obtained from said patient.

13. A method as claimed in claim 12 wherein the step of obtaining the arterial blood volume differential includes the step of non-invasively obtaining blood volume differential with respect to the patient's artery.

14. A method as claimed in claim 13 wherein the step of providing a target value includes the step of obtaining a tissue volume factor about the patient's artery and wherein the step of obtaining arterial blood volume differential includes the step of determining and incorporating a tissue impedance factor therein.

15. A method as claimed in claim 14 wherein the step of providing a target value includes the step of incorporating the chronological age factor, the tissue volume factor and an average systolic blood pressure for an age group about the age of the patient into said first correlation.

16. A method as claimed in claim 15 wherein the step of providing a target value includes the step of incorporating the ascertained cholesterol level as one of an HDL and and LDL value into said first correlation.

17. A method as claimed in claim 16 wherein the step of providing a target value includes the step of providing a look-up table of target values.

18. A method as claimed in claim 17 including the step of providing an operator alarm signal when said representative signal exceeds said predetermined level.

* * * * *